US010518095B2

(12) United States Patent
Ho et al.

(10) Patent No.: US 10,518,095 B2
(45) Date of Patent: Dec. 31, 2019

(54) SYSTEM FOR REPEATED DELIVERY OF IMPLANTABLE DEVICES

(71) Applicant: Pacesetter, Inc., Sunnyvale, CA (US)

(72) Inventors: Friedrich Ho, Mountain View, CA (US); Thomas B. Eby, Mountain View, CA (US); Keith Phillip Laby, Oakland, CA (US)

(73) Assignee: PACESETTER, INC., Sylmar, CA (US)

( * ) Notice: Subject to any disclaimer, the term of this patent is extended or adjusted under 35 U.S.C. 154(b) by 449 days.

(21) Appl. No.: 15/262,968

(22) Filed: Sep. 12, 2016

(65) Prior Publication Data
US 2018/0070983 A1   Mar. 15, 2018

(51) Int. Cl.
| | |
|---|---|
| *A61N 1/375* | (2006.01) |
| *A61N 1/05* | (2006.01) |
| *A61B 17/22* | (2006.01) |
| *A61N 1/372* | (2006.01) |

(52) U.S. Cl.
CPC .................................. *A61N 1/3756* (2013.01)

(58) Field of Classification Search
CPC ................ A61B 17/1214; A61B 17/10; A61B 17/12131; A61B 17/128; A61B 17/3468; A61B 17/32056; A61B 17/221; A61B 2017/1205; A61B 2017/12127; A61B 2017/00367; A61B 2017/22035; A61M 25/0136; A61N 2001/0578; A61F 2/95; A61F 2002/9517
USPC ........................................................ 606/200
See application file for complete search history.

(56) References Cited

U.S. PATENT DOCUMENTS

| 3,943,936 | A |   | 3/1976  | Rasor et al. |   |
|---|---|---|---|---|---|
| 5,114,403 | A | * | 5/1992  | Clarke ................... | A61M 25/01 604/95.04 |
| 5,352,197 | A | * | 10/1994 | Hammersmark ..... | A61M 25/01 600/585 |

(Continued)

FOREIGN PATENT DOCUMENTS

WO      2007/047681      4/2007

*Primary Examiner* — Diane D Yabut
*Assistant Examiner* — Majid Jamialahmadi

(57) ABSTRACT

Disclosed herein is a medical tool adapted to engage and disengage with leadless pacemakers to allow for the repeated use of the tool in delivering and implanting multiple leadless pacemakers into a patient heart in a serial or repeated manner. The tool includes a handle, an attachment mechanism, a torque portion, and a rotation limiter. The handle includes a housing. The attachment mechanism is operably coupled to the housing and configured to actuate between a released state and an engaged state. The torque portion is operably coupled to the housing and rotatable relative to the housing to transition the attachment mechanism between the released and engaged states. The torque portion includes a shaft. The rotation limiter is in sliding engagement with the shaft between a first stop and a second stop. The rotation limiter includes a first helical thread. The tool also includes a second helical thread in threaded engagement with the first helical thread and operably coupled to the housing. Rotation of the torque portion rotates the rotation limiter such that the first helical thread is rotated against the second helical thread, thereby driving the rotation limiter along the shaft between the first stop and the second stop.

22 Claims, 16 Drawing Sheets

(56) References Cited

U.S. PATENT DOCUMENTS

| | | | |
|---|---|---|---|
| 5,601,583 A * | 2/1997 | Donahue | A61B 17/32002 604/22 |
| 7,840,281 B2 | 11/2010 | Kveen et al. | |
| 7,937,148 B2 | 5/2011 | Jacobson | |
| 7,945,333 B2 | 5/2011 | Jacobson | |
| 8,010,209 B2 | 8/2011 | Jacobson | |
| 8,352,025 B2 | 1/2013 | Jacobson | |
| 8,457,742 B2 | 6/2013 | Jacobson | |
| 8,945,145 B2 | 2/2015 | Tran et al. | |
| 8,958,892 B2 | 2/2015 | Khairkhahan et al. | |
| 9,020,611 B2 | 4/2015 | Khairkhahan et al. | |
| 9,126,032 B2 | 9/2015 | Khairkhahan et al. | |
| 9,205,225 B2 | 12/2015 | Khairkhahan et al. | |
| 9,242,102 B2 | 1/2016 | Khairkhahan et al. | |
| 2007/0088397 A1 | 4/2007 | Jacobson | |
| 2007/0088839 A1 | 4/2007 | Jacobson | |
| 2009/0312748 A1 * | 12/2009 | Johnson | A61B 17/12022 606/1 |
| 2010/0010512 A1 * | 1/2010 | Taylor | A61B 17/04 606/144 |
| 2011/0034939 A1 | 2/2011 | Kveen et al. | |
| 2012/0095539 A1 | 4/2012 | Khairkhahan et al. | |
| 2012/0197373 A1 * | 8/2012 | Khairkhahan | A61N 1/3756 607/127 |
| 2015/0018838 A1 | 1/2015 | Nabutovsky et al. | |
| 2016/0067446 A1 | 3/2016 | Klenk et al. | |
| 2016/0067447 A1 | 3/2016 | Paspa et al. | |
| 2016/0096001 A1 | 4/2016 | Eidenschink et al. | |
| 2017/0196594 A1 * | 7/2017 | Sumitro | A61B 17/442 |
| 2017/0319847 A1 | 11/2017 | Ho et al. | |
| 2018/0042552 A1 | 2/2018 | Li et al. | |
| 2018/0050195 A1 | 2/2018 | Knippel et al. | |
| 2018/0168686 A1 | 6/2018 | Jin et al. | |
| 2018/0303514 A1 | 10/2018 | Coyle et al. | |
| 2018/0310949 A1 | 11/2018 | Eby et al. | |
| 2018/0318591 A1 | 11/2018 | Kabe et al. | |
| 2019/0111248 A1 | 4/2019 | Eby et al. | |
| 2019/0134413 A1 | 5/2019 | Mar et al. | |

* cited by examiner

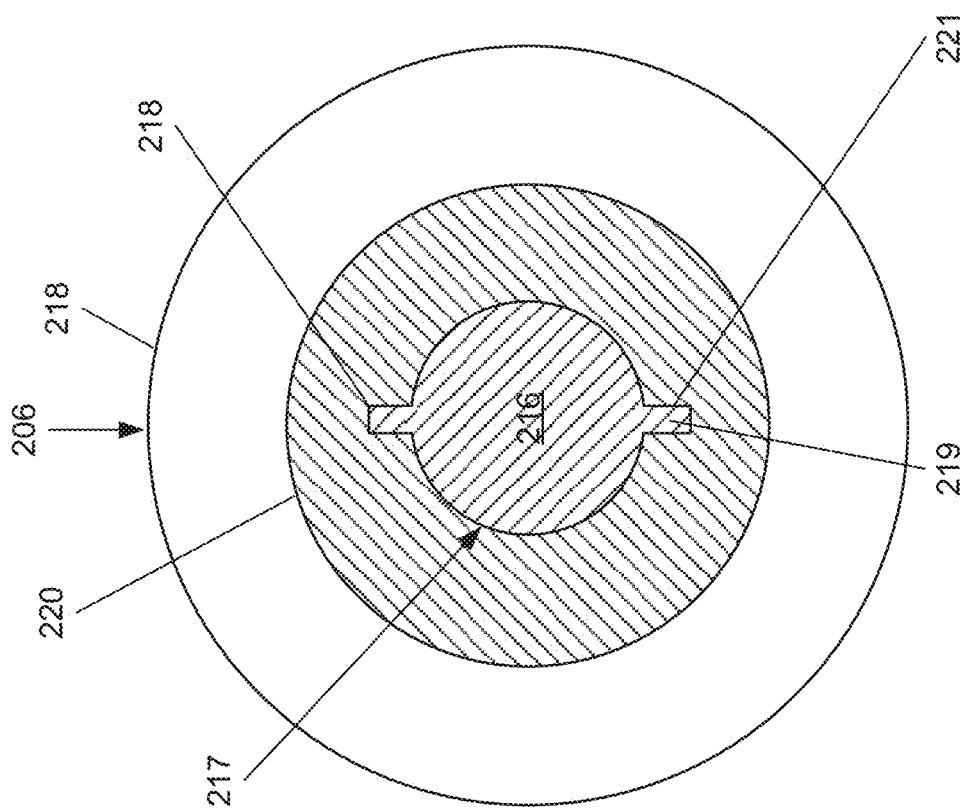
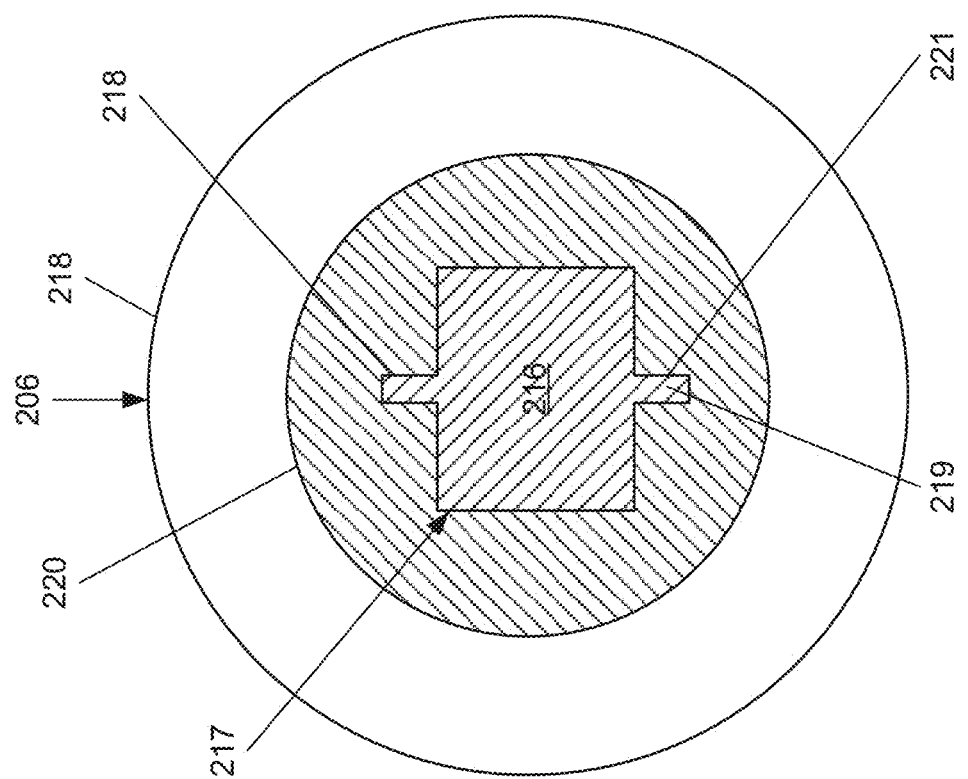

SYSTEM FOR REPEATED DELIVERY OF IMPLANTABLE DEVICES

FIELD OF THE INVENTION

Aspects of the present invention relate to medical apparatus and methods. More specifically, the present invention relates to medical tools and methods for the delivery and implantation of implantable devices, wherein the medical tools can be reused for successive deliveries and implantations of multiple implantable devices.

BACKGROUND OF THE INVENTION

Leadless pacemakers and their delivery systems are a new technology. Current leadless pacemaker delivery systems are single-use and designed to implant a single leadless pacemaker in the patient heart. Once the leadless pacemaker is implanted into the cardiac tissue, the delivery system can no longer be reused for additional implants and must be disposed of. This single-use system configuration is disadvantageous.

For example, if the physician needs to implant multiple leadless pacemakers into the patient, as may be the case with a dual chamber leadless pacemaker arrangement, the physician will require at least two separate delivery systems to deliver both leadless pacemakers. This need for multiple delivery systems results in increased cost to the manufacturer and the end user. Specifically, the manufacturer needs to manufacture and maintain inventory for at least twice as many delivery systems for a dual chamber leadless pacemaker implant, and these additional costs for multiple delivery systems are passed to the end user. This situation results in significant, avoidable costs and waste.

There is a need in the art for a system for delivering multiple leadless pacemakers for implantation in a patient heart, wherein the system is reusable to allow for the delivery of multiple leadless pacemakers. There is also a need in the art for related delivery methods.

BRIEF SUMMARY OF THE INVENTION

Disclosed herein is a medical tool adapted to engage and disengage with leadless pacemakers to allow for the repeated use of the tool in delivering and implanting multiple leadless pacemakers into a patient heart in a serial or repeated manner.

For example, a distal end of the tool includes a lead attachment mechanism that may employ a tether snare that can be increased or decreased in diameter to capture and secure the leadless pacemaker to a docking cap of the distal end of the tool. Alternatively, the lead attachment mechanism may employ two side-by-side parallel tethers each having retention features. The two retention features extend beyond the docking cap of the tool and capture and secure the leadless pacemaker to the docking cap of the distal end of the tool.

In one embodiment, both tethers have an enlarged feature at the distal end (e.g. cylinder with a larger diameter compared to the tether). Both tethers extend distally, such that they are captured within a docking feature (e.g., a thru hole) on a docking button of the leadless pacemaker. When the tether cylinders are aligned, they are of such a combined diameter that they cannot be retracted through the thru hole of the docking button. When the tether cylinders are staggered, they can be retracted through the thru hole of the docking button, which would allow for the leadless pacemaker to separate from the distal end of the tool.

During the release (or staggering) step of the system, one tether remains stationary (referred to as the set tether), while the second tether (referred to as the release tether) travels distally to offset the tether cylinders and release the leadless pacemaker. By operation of a reset mechanism described below in detail, the release tether can be returned to its original position (i.e. the tether cylinders can be realigned or placed in a side-by-side arrangement) to allow the tool to be attached to a second leadless pacemaker for the delivery of the second leadless pacemaker into the patient.

In one embodiment, a handle of the tool includes a torque portion (e.g., release knob) that controls the release tether via a direct drive mechanism (e.g., screw) to effectuate the release tether movement. In one embodiment, the release tether is coupled to a screw-driven mechanism that is connected to the release knob. As the release knob is rotated clockwise, the release tether will travel axially in the distal direction to offset the tether cylinders.

The reset mechanism disclosed herein allows the tool to function as a reloadable delivery system. Specifically, the reset mechanism and its release knob can rotate clockwise and counter-clockwise with excellent and precise control over the number of rotations of the direct drive mechanism and the axial distance travelled by the release tether both distally and proximally relative to the set tether.

In one embodiment, the reloadable delivery system may employ an electro-mechanical, pure mechanical or hydro-electric mechanism that may limit and/or actuate the number of rotations that the release knob can rotate in the clockwise and counter-clockwise directions.

In one embodiment and at the clockwise limit, the release tether can only travel distally a set amount, thus controlling the stagger distance between the release tether and the set tether. Due to the clockwise limit of the reset mechanism disclosed herein, tethers of the attachment mechanism can be predictably and repeatedly placed in an optimized condition for releasing a delivered leadless pacemaker or being staged for engagement with a leadless pacemaker to be secured to the tool for delivery into the patient.

At the counter-clockwise limit, the tether cylinders will be even (i.e., in a side-by-side arrangement), thus returning the delivery system to an optimized state in which a leadless pacemaker can be most secured to the docking cap of the tool for delivering the leadless pacemaker to an implantation site in the patient. Thus, in one embodiment, the attachment mechanism may be repeatedly transitioned between an engaged state and a disengaged state such that the loading of a leadless pacemaker can begin with the release tether in the staggered setting and inserted into and received by a docking feature of the leadless pacemaker. The attachment mechanism can then be transitioned such that the release tether is caused to become side-by-side with the set tether while the tether features are located within the boundaries of the docking feature of the leadless pacemaker, the combined diameter of the side-by-side tether features being too great to allow the attachment mechanism to be released from the docking feature of the leadless pacemaker.

Repeatability of attaining this optimized "even" or "side-by-side" state after initial leadless pacemaker release is desirable for a delivery system employing dual tethers or other attachment mechanisms, such a tether snare. For example, failure of the tether features to be perfectly side-by-side when in the engaged state by any amount of more than 0.005" may cause difficulties in appropriately delivering the leadless pacemaker to the target site. The precision offered by the reset mechanism disclosed herein is especially desirable in view that the percutaneous delivery systems are often times long (many feet long), soft, flexible, semi-compliant systems that balance competing mechanical requirements of being both soft enough to not harm the vasculature of a patient and stiff enough to be controlled in a precise manner to target implant locations.

Beyond the advantage of using one delivery system to implant multiple devices, an additional benefit to implementing a clockwise limitation is that it reduces user error with regards to how far the release tether can stagger. Excessive stagger may lead to difficulty separating the leadless pacemaker from the delivery system as the tether cylinder may extend and interact with various leadless pacemaker features or other structures, increasing the difficulty with which the leadless pacemaker can separate from the delivery system.

An advantage of the reset mechanism is it allows the reliable and consistent resetting the release tether to its original optimized engaged and released states multiple times, such that any number of leadless pacemakers may be retained and released by the delivery system.

In one embodiment, a proximal portion of the handle includes the reset mechanism, which employs a rotation limiter mechanism that limits the number of rotations that the release knob can rotate clockwise and counter-clockwise. In this embodiment, the rotation limiter mechanism may include a stationary hexagonal nut that is retained with the proximal portion of the handle and an axially sliding threaded rotation limiter linked to the release knob. The rotation limiter may be independent of the screw driven mechanism that drives the release tether. However, in other embodiments, the rotation limiter and screw driven mechanism that drives the release tether may be combined into one assembly.

The release knob may be operably linked to the release tether via a shaft, the release knob being rotationally linked to the shaft via a keyed geometric feature (e.g. square, hexagon, octagon, male-female interface, etc.) of the shaft. Rotation of the release knob causes the shaft to rotate, which causes the direct drive mechanism of the release tether to rotate within a separate threaded housing within the handle. This rotation causes the release tether to move distal-proximal relative to the set tether.

During rotation of the release knob, the rotation limiter of the rotation limiter mechanism travels distal-proximal within the threaded hex nut and abuts a physical stop at the proximal and distal position, depending on which direction the rotation limiter is being caused to displace. These physical stops limit the number of rotations of the release knob and also allow for the release knob, and more specifically, the attachment mechanism to return to its released and engaged states with reliable and predictable consistency.

In one embodiment, the rotation limiter includes of a left-handed thread. That is, the rotation limiter will travel proximally as the release knob is rotated clockwise, thereby causing the release tether to translate to the staggered position relative to the set tether. Also, the rotation limiter will travel distally as the release knob is rotated counter-clockwise, thereby causing the release tether to translate to the side-by-side position with the set tether.

In one embodiment, the physical stop on the distal limit of travel may be a raised geometric feature on the hex nut that interacts with a pin on the flange of the rotation limiter. The physical stop on the proximal limit of travel may occur when the proximal portion of the flange bottoms out against the interior of the handle half.

The purpose of the left handed thread is to ensure a reliable and consistent method for the release tether to realign with the set tether. Due to the timing required to ensure that the flange of the rotation limiter resets to the same position every time with respect to the hex nut (i.e. 100% reliability to realign tethers), the physical stop of the distal limit can be manufactured with greater consistency. Furthermore, the rotation limit mechanism, which includes the rotation limiter and the hex nut, can be manufactured as a subassembly, thus ensuring that the distal limit is accurate and reliable.

In one embodiment, the proximal limit may be housed in the proximal portion of the handle. Other embodiments of the design may include alternate concepts of the proximal and distal physical stops, which would allow for a standard right hand thread on the rotation limiter. In addition and in some embodiments, the features (e.g., physical stops and threads) of the hex nut may be designed directly onto the proximal portion of the handle.

In one embodiment, the delivery system may also include a tether position indicator to provide a visual cue to the state of the release tether. The tether position indicator may include a cylindrical pin that protrudes from the surface of the handle when the release tether is staggered and is flush with the surface of the handle when the release tether is aligned with the set tether.

In one embodiment, the tether position indicator rides on the surface of a flange of the rotation limiter. Specifically, a cam feature present on the tether position indicator allows for its position to alternate between raised and flush as the rotation limiter travels distal-proximal within the proximal portion of the handle.

In one embodiment, the tether position indicator may be spring loaded in order to ensure that its position is consistent with the tether position regardless of handle orientation (e.g. if the proximal handle is upside down, the spring would ensure the tether position indicator remains flush with the handle surface).

In one embodiment, the material of the tether position indicator may a low coefficient of friction. Since the tether position indicator slides against the flange of the rotation limiter, the two surfaces have a bearing surface. High friction materials can create a non-ideal tactile feel as the user translates the release tether (e.g. galling of metal surfaces). In one embodiment, the tether position indicator and rotation limiter are manufactured from polyetheretherketone (PEEK) or another engineered plastic material with a low coefficient of friction.

Alternate embodiments to the tether position indicator may include, but are not limited to, axially sliding indicators with obvious markings on the proximal portion of the handle or colorimetric indicators. Furthermore, electronic indicators may also be used, which may include, but not limited to, electronic indicators (e.g LEDs or software icons) on the proximal portion of the handle or external displays or consoles.

In one embodiment, the tool includes a handle, an attachment mechanism, a torque portion, and a rotation limiter. The handle includes a housing. The attachment mechanism is operably coupled to the housing and configured to actuate between a released state and an engaged state. The torque portion is operably coupled to the housing and rotatable relative to the housing to transition the attachment mechanism between the released and engaged states. The torque portion includes a shaft. The rotation limiter is in sliding engagement with the shaft between a first stop and a second stop. The rotation limiter includes a first helical thread. The tool also includes a second helical thread in threaded engagement with the first helical thread and operably coupled to the housing. Rotation of the torque portion rotates the rotation limiter such that the first helical thread is rotated against the second helical thread, thereby driving the rotation limiter along the shaft between the first stop and the second stop.

In one embodiment, the attachment mechanism reaches the released state when the rotation limiter reaches the first stop, and the attachment mechanism reaches the engaged state when the rotation limiter reaches the second stop.

In one embodiment, the tool further includes a drive mechanism supported by the housing and operably coupling the torque portion to the attachment mechanism.

In one embodiment, the tool further includes a ratchet mechanism that gives feedback (e.g., a tactile indication) when torque portion is rotated.

In one embodiment, the tool further includes a position indicator configured to indicate when the rotation limiter reaches at least one of the first stop or second stop. For example, the position indicator may include a cam configuration that interacts with the rotation limiter to indicate when the rotation limiter has reached at least one of the first stop or second stop. Also by way of example, the position indicator may include at least one of an axially sliding indicator, an electronic indicator, or a radially displacing indicator.

In one embodiment, the shaft includes a transverse cross-section including a non-circular outer surface along which the rotation limiter can slide but linking the shaft and the rotation limiter together to rotate together as a unit.

For example, the shaft may extend through a hole in the rotation limiter, the hole including a shape that is a negative of the non-circular outer surface. The non-circular outer surface of the transverse cross-section may be in the form of one of an ellipse, square, rectangle, trapezoid, diamond, triangle, pentagon, hexagon, octagon or any of a host of other non-circular shapes.

In one embodiment, the shaft and the rotation limiter include a keyed interface that allows the rotation limiter to slide along the shaft but results in the shaft and rotation limiter rotating together as a unit. For example, the keyed interface may include a non-circular outer transverse cross-section of the shaft and a complementary negative surface of the rotation limiter that interfaces with the non-circular outer transverse cross-section of the shaft. Additionally or alternatively, the keyed interface may include a male-female interface including a male feature on one of the shaft or rotation limiter and a female feature on the other of the shaft or rotation limiter, the male feature being received in the female feature.

In one embodiment, the attachment mechanism includes a tether snare that has a first diameter when the attachment mechanism is in the released state and a second diameter when the attachment mechanism is in the engaged state, the second diameter being smaller than the first diameter.

In one embodiment, the attachment mechanism includes a pair of tethers, each tether including a tether member, wherein the tether members are longitudinally offset from each other when the attachment mechanism is in the released state and the tether members are longitudinally even with each other and in a side-by-side arrangement when in the attachment mechanism is in the engaged state.

In one embodiment, the medical tool is configured to deliver a leadless pacemaker to an implantation site in a patient and includes a handle, an elongated body, an attachment mechanism, a torque portion, and a rotation limiter. The handle includes a housing, and the elongated body distally extends form the handle. The attachment mechanism is near a distal end of the elongated body and configured to actuate between a first state and a second state. When the attachment mechanism is in the first state, the attachment mechanism is configured to secure the leadless pacemaker to the tool. When the attachment mechanism is in the second state, the attachment mechanism is configured such that the leadless pacemaker will not secure to the tool. The torque portion is operably coupled to the housing and rotatable relative to the housing to transition the attachment mechanism between the first and second states. The torque portion includes a shaft. The rotation limiter includes a first helical thread. The rotation limiter interfaces with the shaft such that the rotation limiter can slide along the shaft between a first stop and a second stop, but the shaft and the rotation limiter rotate together as a unit. The tool also includes a second helical thread in threaded engagement with the first helical thread and fixed relative to the housing. Rotation of the torque portion rotates the rotation limiter such that the first helical thread is rotated against the second helical thread, thereby driving the rotation limiter along the shaft between the first stop and the second stop.

In one embodiment, the attachment mechanism reaches the first state when the rotation limiter reaches the first stop, and the attachment mechanism reaches the second state when the rotation limiter reaches the second stop.

In one embodiment, the tool further includes a position indicator configured to indicate when the rotation limiter reaches at least one of the first stop or second stop.

In one embodiment, the interfacing between the shaft and the rotation limiter includes a non-circular outer transverse cross-section of the shaft and a complementary negative surface of the rotation limiter that interfaces with the non-circular outer transverse cross-section of the shaft.

In one embodiment, the interfacing between the shaft and the rotation limiter includes a male-female arrangement including a male feature on one of the shaft or rotation limiter and a female feature on the other of the shaft or rotation limiter, the male feature being received in the female feature.

In one embodiment, the attachment mechanism includes a tether snare that has a first diameter when the attachment mechanism is in the first state and a second diameter when the attachment mechanism is in the second state. The second diameter is larger than the first diameter.

In one embodiment, the attachment mechanism includes a pair of tethers, each tether including a tether member. The tether members are longitudinally offset from each other when the attachment mechanism is in the second state and the tether members are longitudinally even with each other and in a side-by-side arrangement when in the attachment mechanism is in the first state.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIGS. 5M-5P illustrate examples of a keyed interface between the shaft and the rotation limiter.

DETAILED DESCRIPTION

Figure 1:
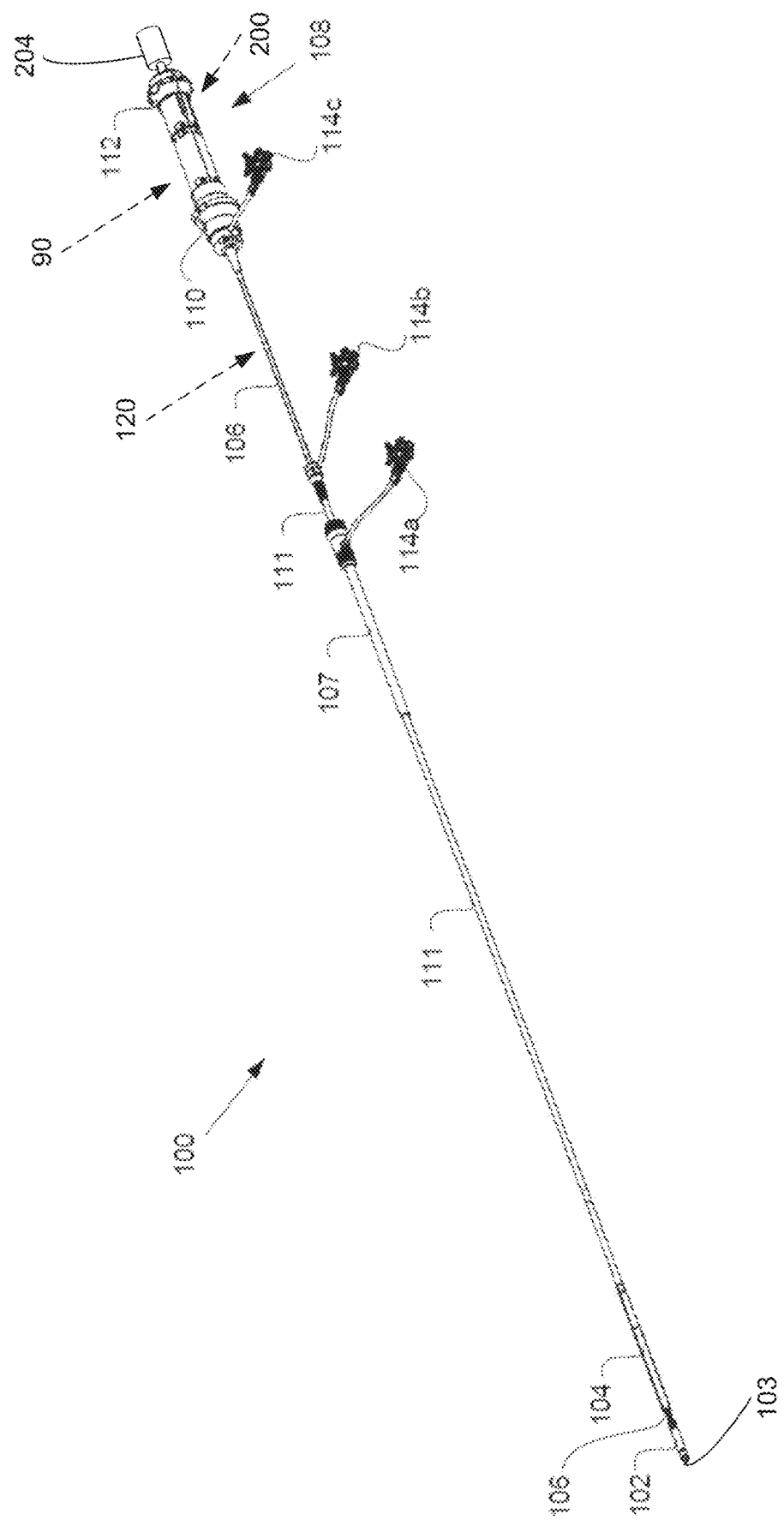
FIG. 1 is an isometric view of an example of a leadless pacemaker delivery system that can be reused for successive deliveries and implantations of multiple leadless pacemakers.

Implementations of the present disclosure involve a medical tool. In one embodiment, the medical tool is a leadless pacemaker delivery system 100 that includes a reset mechanism 200 that limits the displacement of an attachment mechanism 122 between an ideal or preferred engaged state and an ideal or preferred released state. Although the attachment mechanism 122 may take on a variety of configurations, depending on the embodiment, it is ultimately configured to engage and disengage in a predictable and repeatable manner the leadless pacemaker. The reset mechanism 200 of the leadless pacemaker delivery system 100 is used to predictably and repeatedly place the delivery system, and more specifically its attachment mechanism, into appropriate conditions such that leadless pacemakers can be repeatedly loaded onto, delivered and deployed via the delivery system to facilitate successive deliveries and implantations of multiple leadless pacemakers via a single delivery system.

Before discussing the specifics of the reset mechanism disclosed here, a discussion will now be provided regarding an example medical tool employing the reset mechanism in the context of delivery of a leadless pacemaker.

A. Overview of Example Tool Embodiments Employing the Reset Mechanism

The reset mechanism 90 disclosed herein and discussed in detail below may be beneficially employed in a wide variety medical tools. For example, in one embodiment, the reset mechanism 90 may be employed in the handle 108 of a leadless pacemaker delivery system 100 configured to deliver into a patient a leadless pacemaker 102 such as the NANOSTIM™ leadless pacemaker as manufactured by St. Jude Medical, Inc.

Typically, a leadless pacemaker is substantially enclosed in a hermetic housing suitable for placement on or attachment to the inside or outside of a cardiac chamber. Depending on the embodiment, the pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a leadless pacemaker can be adapted for delivery and implantation into tissue in the human body. In a particular embodiment, a leadless pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Self-contained or leadless pacemakers or other biostimulators are typically fixed to an intracardial implant site by an actively engaging mechanism or primary fixation mechanism such as a screw or helical member that screws into the myocardium. Examples of such leadless biostimulators are described in the following publications, the disclosures of which are incorporated by reference herein in their entireties: (1) U.S. Pat. No. 8,457,742; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 19, 2007; (4) U.S. Pat. No. 8,352,025; (5) U.S. Pat. No. 7,937,148; (6) U.S. Pat. No. 7,945,333; (7) U.S. Pat. No. 8,010,209; and (8) International Application No. PCT/US2006/040564, filed on Oct. 13, 2006, entitled "Leadless Cardiac Pacemaker and System" and published as WO07047681A2 on Apr. 26, 2007.

Leadless pacemakers or biostimulators can be delivered to, and retrieved from, a patient using a delivery system 100 similar to that described below with respect to FIG. 1, which is an isometric view of the delivery system 100. As illustrated in FIG. 1, the delivery system 100 can include a guide catheter sheath 111 including an atraumatic distal end 104 in the form of a pacemaker sheath 104. The delivery system 100 can also have a pacemaker introducer sheath 107 and a catheter shaft 106. The catheter shaft 106 includes at its proximal end the handle 108, a deflection knob 110, and a tether shuttle 112. Each of the longitudinal bodies 107, 111, 106 includes a flush port 114a, 114b, 114c extending respectively therefrom. As can be understood from FIG. 1, the catheter shaft 106 extends through the guide catheter sheath 111, which extends through the introducer sheath 107. Each of the longitudinal bodies 106, 107, 111 are displaceable proximal-distal relative to each other.

As discussed in detail in U.S. patent application Ser. No. 14/508,556, which is entitled "DELIVERY CATHETER SYSTEMS AND METHODS", was filed Oct. 7, 2014, and is hereby incorporated by reference in its entirety herein, in one embodiment, the atraumatic pacemaker sheath 104 may have a braided or woven construction that is sufficiently flexible to allow the atraumatic pacemaker sheath 104 to encompass the leadless pacemaker 102 or to have a diameter that is smaller than a diameter of the leadless pacemaker 102 when not encompassing the leadless pacemaker 102. The deflection knob 110 can be used to deflect the catheter shaft 106 within the catheter sheath 111 to steer and guide the catheter during implantation and/or removal of the pacemaker. The flush ports 114a, 114b, and 114c can be used to flush saline or other fluids through the catheter. The atraumatic sheath 104 forms the distal most region of the catheter sheath 111. The catheter sheath 111 can be advanced distally over the catheter shaft 106 such that the atraumatic sheath 104 is caused to extend over the leadless pacemaker 102. Also, the distal displacement of catheter sheath 111 relative to the catheter shaft 106 can be used to provide additional steering and support for the delivery catheter during implantation and to surround the pacemaker as it is introduced through a trocar or the introducer sheath 107 into the patient. The catheter sheath 111 can be retracted proximally over the catheter shaft 106 such that the atraumatic sheath 104 is caused to retract from over the leadless pacemaker 102, the braided construction of atraumatic sheath 104 being such that the atraumatic sheath 104 self-biases into a reduced diameter. The reduced diameter of the atraumatic sheath 104 is no greater than the diameter of the leadless pacemaker 102.

As can be understood from FIG. 1 and the above-referenced patent/applications, a leadless pacemaker 102 is attached or connected to a distal end of the delivery system 100 and advanced intravenously into the heart to an implantation location in the heart where the tissue anchor or screw 103 of the leadless pacemaker 102 can be caused to anchor the leadless pacemaker to the heart tissue. In one embodiment, a rotation mechanism 90 incorporated in the handle 108 of the delivery system 100 can be used to cause a linear member 120 that extends longitudinally through the catheter shaft 106 and is operably coupled to the rotation mechanism 90 to rotate relative to the catheter shaft 106 about the longitudinal axis of the catheter shaft 106 to rotate the leadless pacemaker 102 about its longitudinal axis such that the distal helical anchor 103 of the leadless pacemaker 102 screws into the cardiac tissue if the leadless pacemaker 102 is being implanted or to unscrew from the cardiac tissue if the leadless pacemaker 102 is being explanted.

Figure 2:
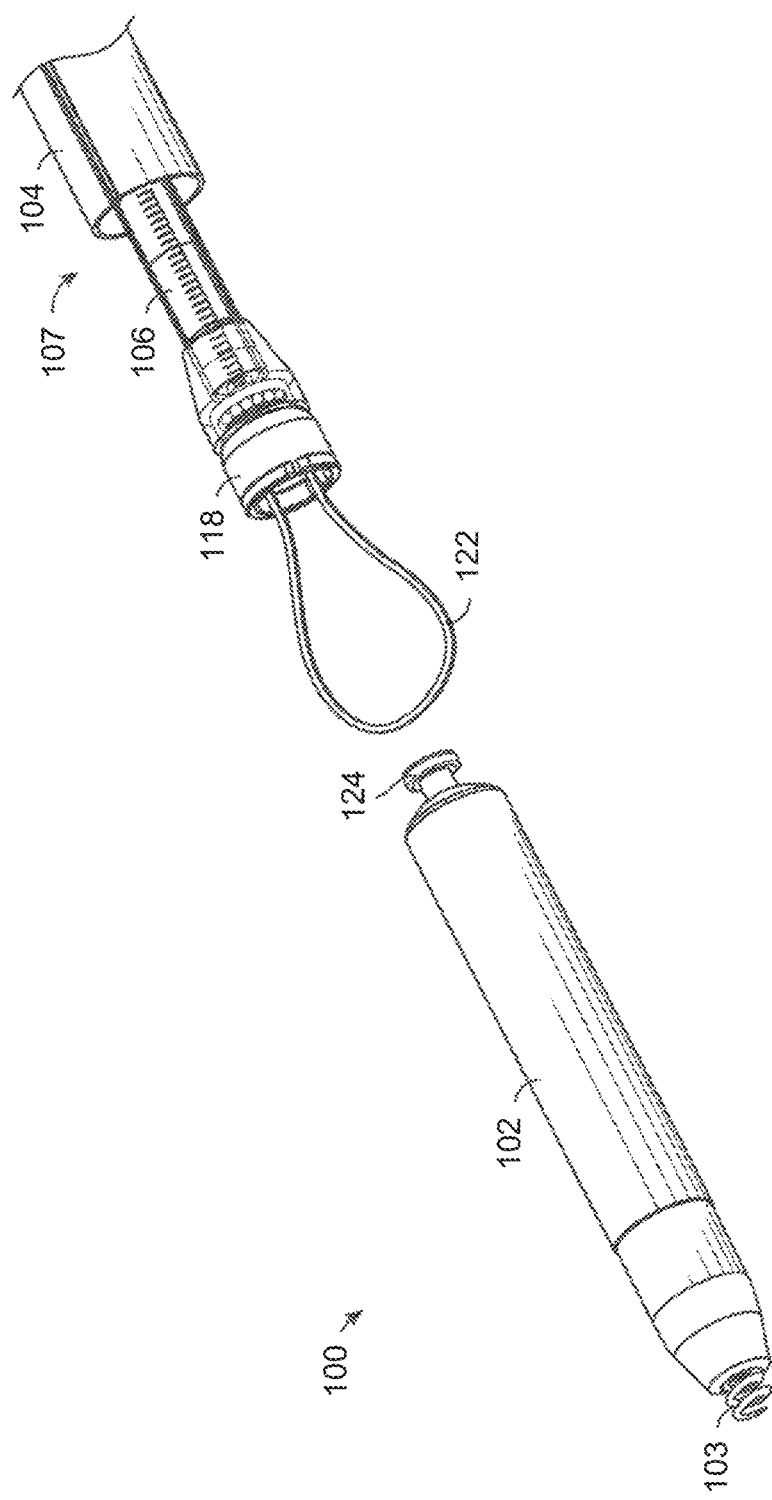
FIG. 2 is an isometric view of the distal end of the catheter shaft of the delivery system in close proximity to the leadless pacemaker, the distal end of the catheter shaft having a docking cap and an attachment mechanism extending therefrom in the form of a tethering snare positioned to engage an attachment member of the leadless pacemaker.
Figure 3A:
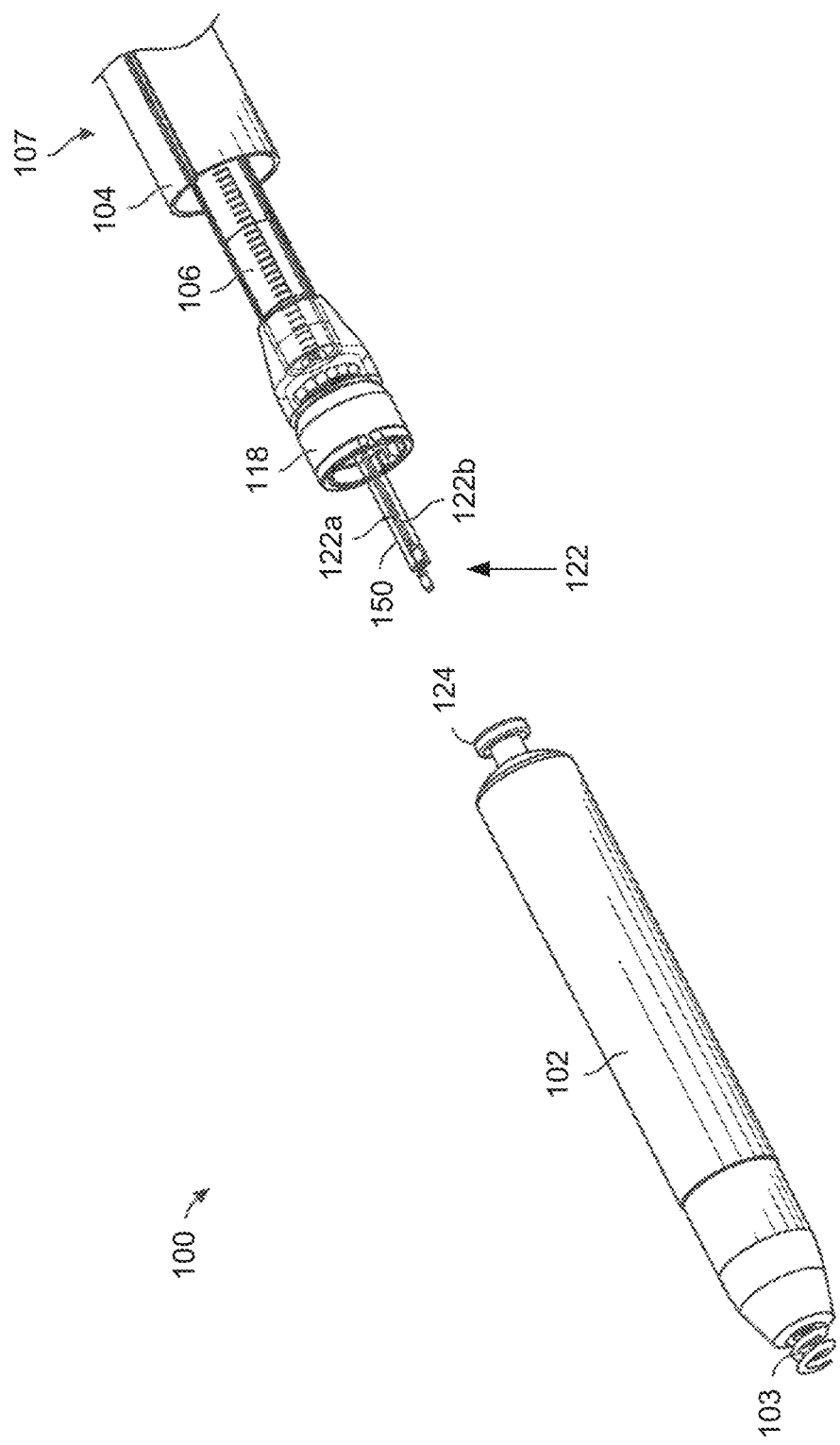
FIG. 3A is an isometric view of the delivery system distal end in close proximity to the leadless pacemaker, the distal end of the delivery system having an attachment mechanism in the form of a tethering snare positioned to engage an attachment member of the leadless pacemaker.

There are a variety of arrangements for attaching or connecting the leadless pacemaker to the distal end of the delivery system 100. For example, as shown in FIG. 2, which is an isometric view of the distal end of the catheter shaft 106 of the delivery system 100 in close proximity to the leadless pacemaker 102, the distal end of the catheter shaft 106 has a docking cap 118 and an attachment mechanism 122 extending therefrom in the form of a tethering snare 122 positioned to engage an attachment member 124 of the leadless pacemaker 102. As discussed in detail in U.S. patent application Ser. No. 14/481,818, which is titled "SYSTEMS AND METHODS FOR IMPLANTING A MEDICAL DEVICE", was filed Sep. 9, 2014, published Mar. 10, 2016 as US 2016/0067446 A1, and is hereby incorporated in its entirety into this present disclosure, the tether snare 122 can be used to lasso the attachment member 124 of the leadless pacemaker 102 to dock the proximal end of the leadless pacemaker with the docking cap 118 at the distal end of the catheter shaft 106. Thus, the tether snare 122 forms an attachment mechanism that is configured to actuate between a released state and an engaged state. In other words, the attachment mechanism includes a tether snare 122 that has a first diameter when the attachment mechanism is in the released state and a second diameter when the attachment mechanism is in the engaged state, the second diameter being smaller than the first diameter As illustrated in FIG. 3A, which is an isometric view of the distal end of the catheter shaft 106 of another embodiment of the delivery system 100 in close proximity to the leadless pacemaker 102, the distal end of the catheter shaft 106 has a docking cap 118 and an attachment mechanism 122 extending therefrom in the form of a pair of tethers 122a, 122b longitudinally offset from each other to engage an attachment member 124 of the leadless pacemaker 102. As discussed in detail in U.S. patent application Ser. No. 14/481,799, which is titled "IMPLANTABLE MEDICAL DEVICE HAVING RESTRAINED TETHER DEVICE", was filed Sep. 9, 2014, published Mar. 10, 2016 as US 2016/0067447 A1, and is hereby incorporated in its entirety into this present disclosure, the tethers 122a, 122b each distally terminate as tether members 126a, 126b and are confined in an internal passage 154 of a flexible longitudinal body 152 of a restrainer 150 distally projecting out of the docking cap 118, as can be understood from FIGS. 3B and 3C.

Figure 3B:
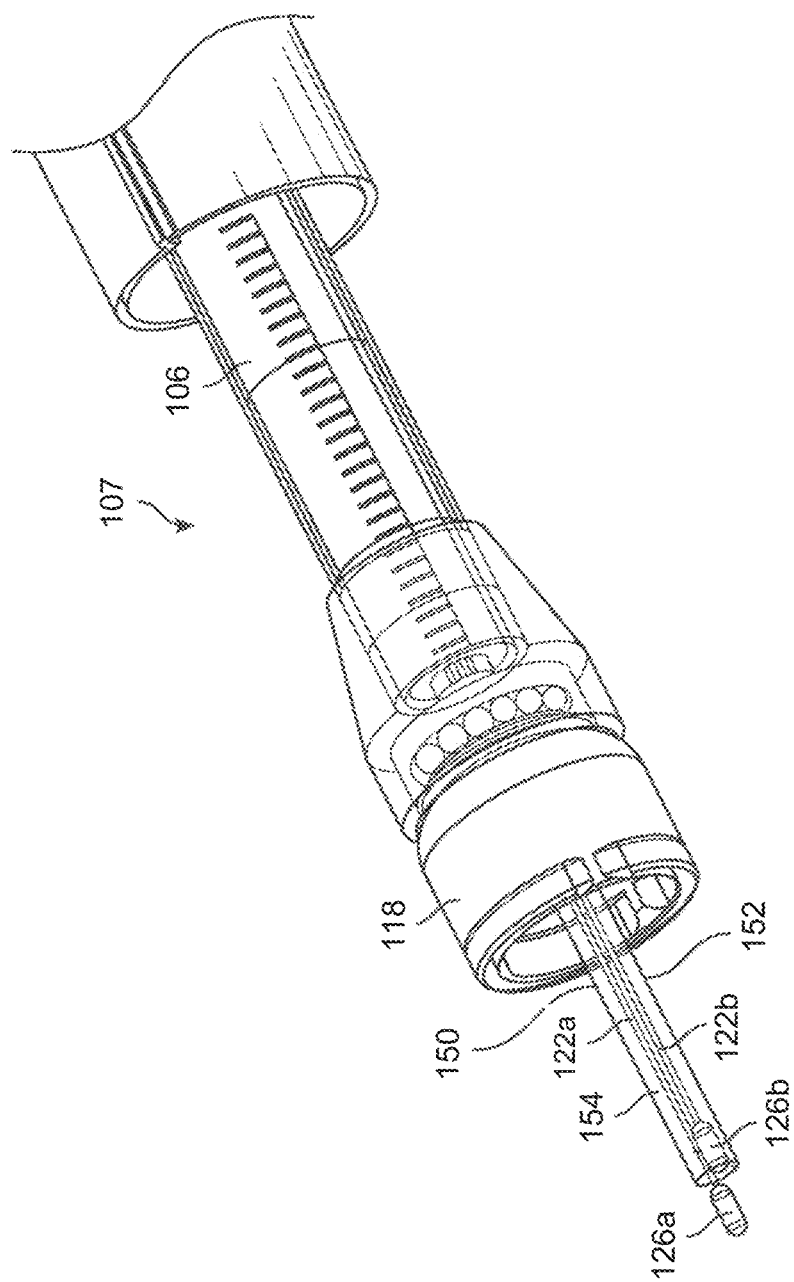
FIG. 3B is an enlarged isometric view of the delivery system distal end of FIG. 3A, wherein the tethers are longitudinally offset relative to each other.
Figure 3C:
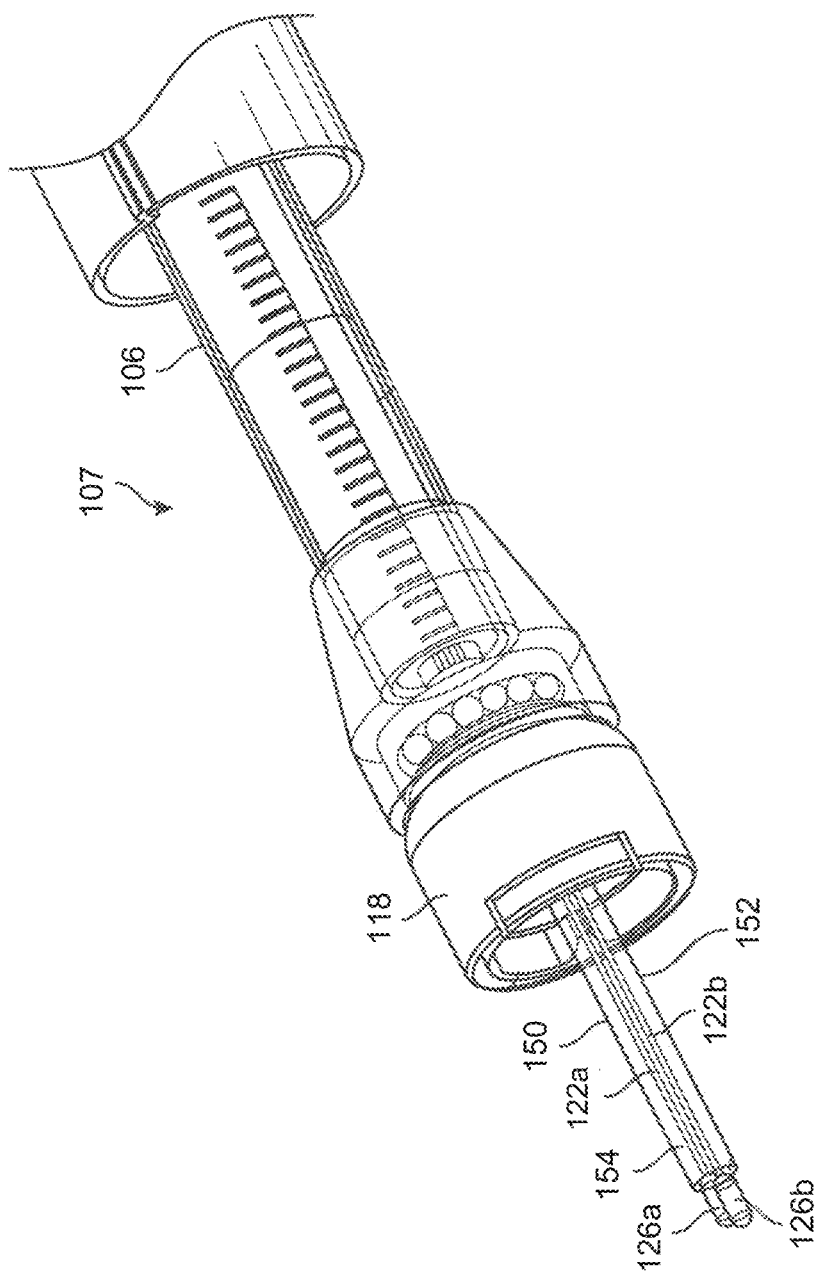
FIG. 3C is an enlarged isometric view of the delivery system distal end of FIG. 3A, wherein the tethers are not longitudinally offset relative to each other.
Figure 3D:
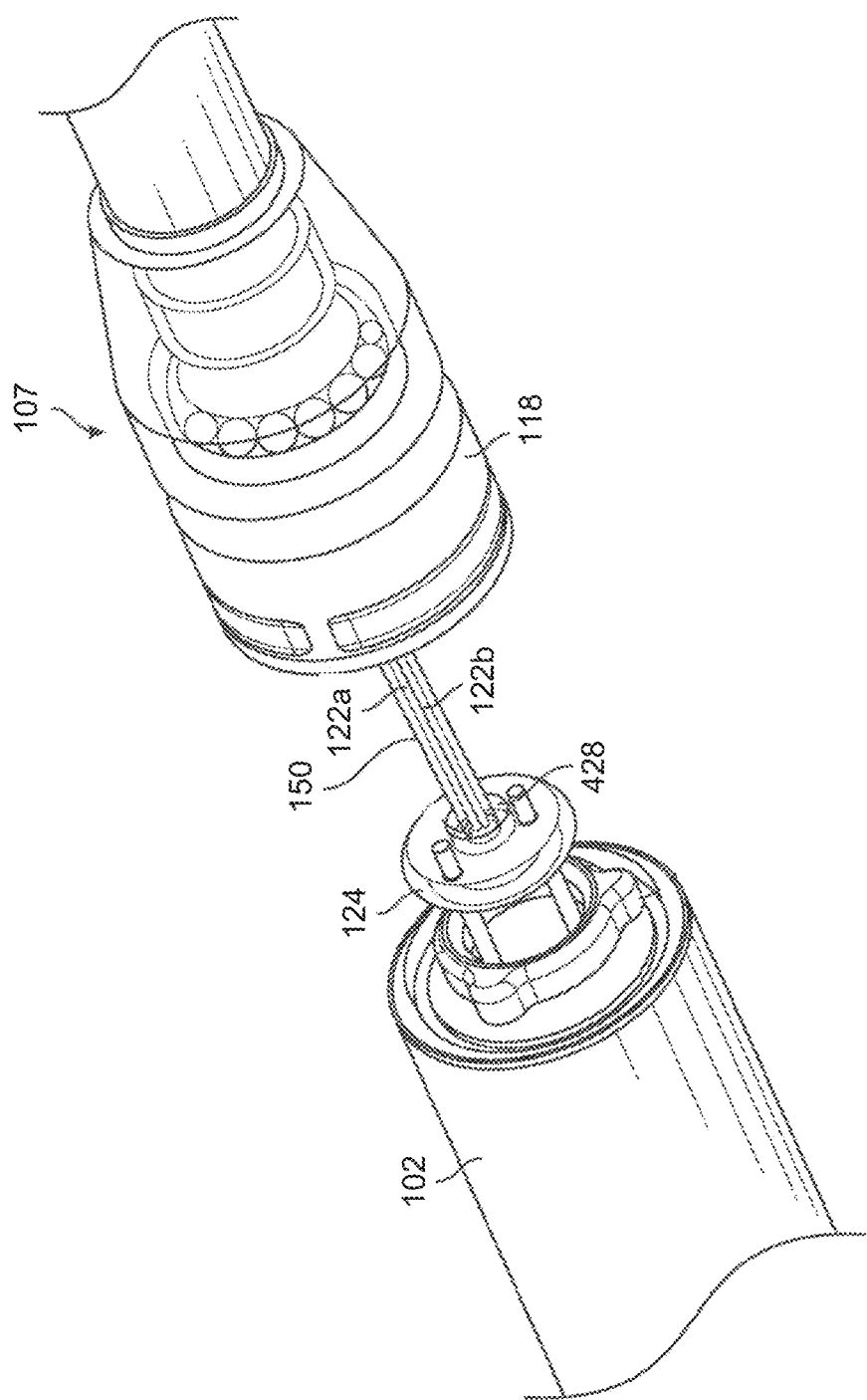
FIG. 3D is an enlarged isometric view of the delivery system distal end of FIG. 3A and further illustrating the tethers being received through a hole in an attachment member of the proximal end of the leadless pacemaker of FIG. 3A.

As indicated in FIG. 3B, the tethers 122a, 122b can be longitudinally offset relative to each other such that the tether members 126a, 126 are longitudinally staggered relative to each other. As a result, the tethers 122a, 122b have a combined lateral diameter that is sufficiently small to be received through the hole 428 in the leadless pacemaker attachment member 124, as can be understood from FIG. 3D. Once the tethers 122a, 122b are no longer longitudinally offset relative to each other, as shown in FIG. 3C, the tether members 126a, 126b are no longer longitudinally staggered relative to each other and form a combined lateral diameter that is greater than the diameter of the hole 428, thereby securing the tethers 122a, 122b to the attachment member 124 of the leadless pacemaker 102.

Thus, the tethers 122a, 122b form an attachment mechanism that is configured to actuate between a released state and an engaged state. In other words, the attachment mechanism includes a pair of tethers 122a, 122b, each tether 122a, 122b including a tether member 126a, 126b, wherein the tether members are longitudinally offset from each other when the attachment mechanism is in the released state (see FIG. 3B) and the tether members are longitudinally even with each other and in a side-by-side arrangement when in the attachment mechanism is in the engaged state (see FIG. 3C).

It should be understood that the attachment mechanisms 122 disclosed herein are not limited to a dual tether based system or a tether snare system. Alternate attachment mechanisms could benefit from the herein disclosed binary mechanisms to release and retain implantable devices, such as leadless pacemakers, the binary mechanisms including proximal and distal limits to control the attachment mechanism between optimized engaged and released states. For example, in one embodiment, the attachment mechanism 122 may employ a continuous loop with a breakaway feature at a distal end of the loop. The breakaway feature may be activated by axial translation of a single leg of the loop until its breaks free from the opposite leg of the loop. The loop may be reset by reversing the axial translation of the single leg on the loop and resetting the breakaway feature.

To facilitate the delivery system 100 being reused for successive deliveries and implantations of multiple leadless pacemakers 102, the delivery systems disclosed herein employ reset mechanisms 200 as described in detail below. These reset mechanisms 200 allow the various attachment mechanisms 122 of the delivery systems 100 to be actuated in such a manner that the attachment mechanisms 122 can predictably and repeatedly connect and disconnect from the attachment members 124 of the leadless pacemakers 102.

B. Handle with Reset Mechanism Employing Thread Limiter

Figure 4:
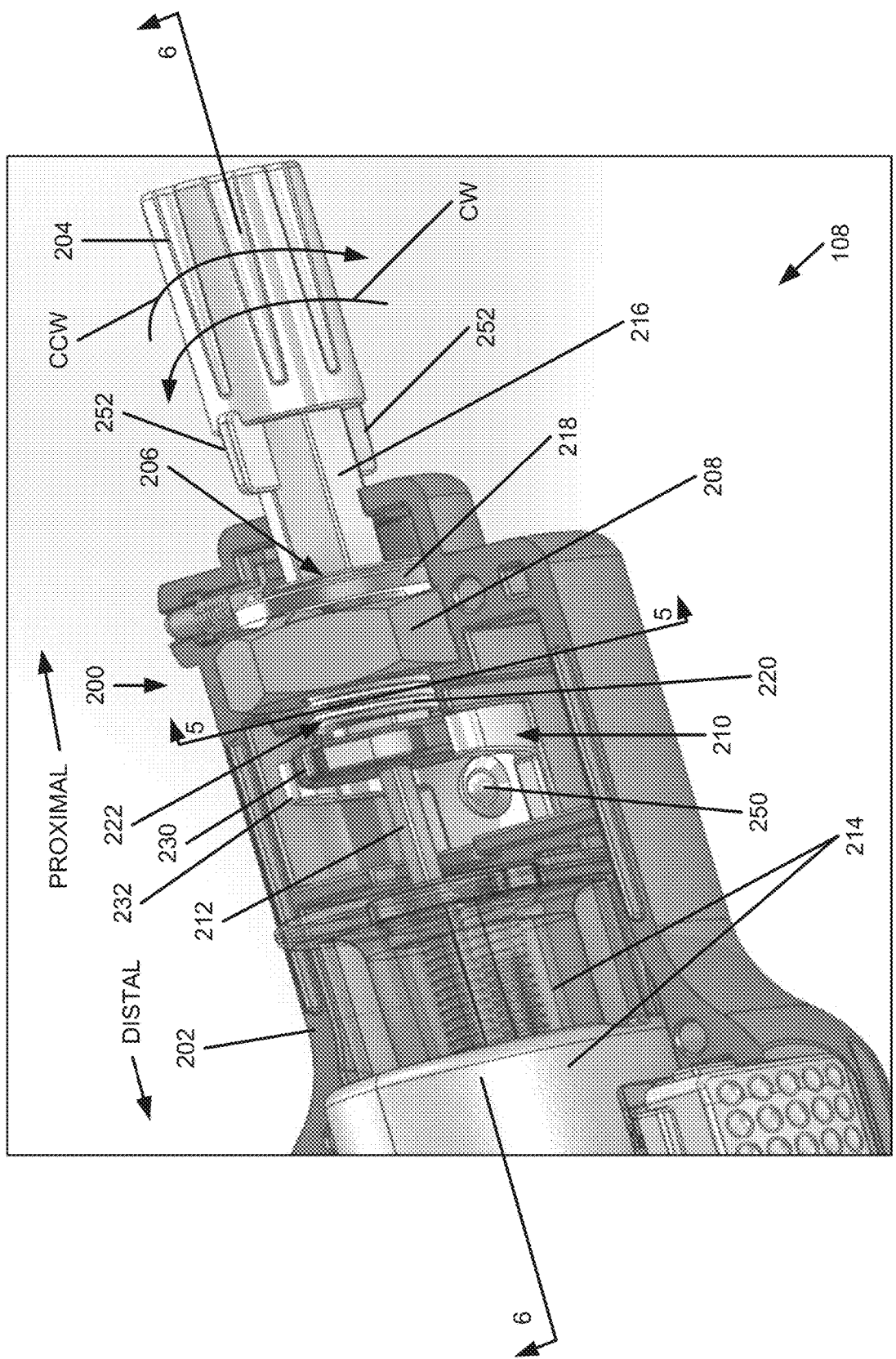
FIG. 4 is an isometric view of the proximal region of the handle of the leadless pacemaker delivery system of FIG. 1 with a portion of the housing of the handle removed to reveal the components of the reset mechanism contained therein.

FIG. 4 is an isometric view of the proximal region of the handle 108 of the leadless pacemaker delivery system 100 of FIG. 1 with a portion of the housing 202 of the handle 108 removed to reveal the components of the reset mechanism 200 contained therein. The reset mechanism 200 is used to predictably and repeatedly place the delivery system 100, and more specifically, its attachment mechanism 122 into appropriate conditions (e.g., the above-described released state and engaged state) such that leadless pacemakers 102 can be repeatedly loaded onto, delivered and deployed via the delivery system 100 to facilitate successive deliveries and implantations of multiple leadless pacemakers 102 via a single delivery system 100.

As shown in FIG. 4, the handle 108 includes the housing 202 and a torque portion 204, which may be in the form of a torque knob 204. The housing 202 encloses some of the reset mechanism 200. The handle 108 and its housing 202 are coupled to the catheter shaft 106, as can be understood from FIG. 1. The torque portion 204 is operably coupled to the housing 202 such that the torque portion 204 can rotate relative to the housing 202 about a common longitudinal axis of the two elements 202, 204.

As illustrated in FIG. 4, the reset mechanism 200 includes the torque portion 204, a rotation limiter 206, a threaded receptacle 208, a ratchet mechanism 210 and a drive shaft 212 that extends distally from the rest of the reset mechanism 200 to a direct drive mechanism 214. The direct drive mechanism 214 transmits rotation of the drive shaft 212 to the requisite displacement of the attachment mechanism 122 between the above-described released and engaged states of the attachment mechanism 122.

The torque portion includes a shaft 216. As can be understood from FIG. 4, in one embodiment, the shaft 216 includes a transverse cross-section including a non-circular outer surface along which the rotation limiter 206 can slide distal-proximal along the shaft, but linking the shaft and the rotation limiter together to rotate together as a unit.

Specifically, as can be understood from FIGS. 5A-5L, which are transverse cross sections through the shaft 216 and the rotation limiter 206 as taken along section line 5-5 in FIG. 4, the shaft 216 extends through a hole 217 in the rotation limiter 206. The hole 217 includes a shape that is a negative of the non-circular outer surface of the shaft 216. For example, the non-circular outer surface of the transverse cross-section is shown in FIG. 4 to have multiple planar side faces, which, as respectively shown in FIGS. 5A-5L may define an outer boundary of the cross-section in the form of a triangle, rectangle, square, rounded corner rectangle, rounded square, ellipse, pentagon, hexagon, heptagon, octagon, star-shaped, cross-shaped, or etc. Of course, the shapes indicated in FIGS. 5A-5L are merely examples, and the outer boundary of the cross-section may be in the form any other geometric or complex shape that would still allow the rotation limiter 206 to displace distal-proximal along the shaft 216 but require the rotation limiter 206 and shaft 216 to rotate about the longitudinal center axis of the shaft 216 as a unit.

Figure 5A:
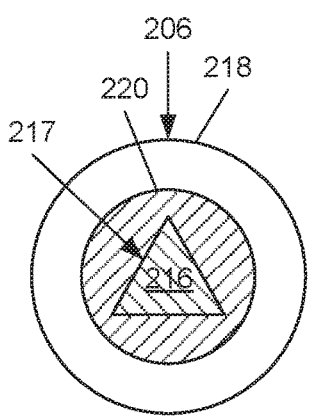
FIGS. 5A-5L are transverse cross sections through the shaft and the rotation limiter as taken along section line 5-5 in FIG. 4, FIGS. 5A-5L respectively showing shaft transverse cross-sections that are in the form of a triangle, rectangle, square, rounded corner rectangle, rounded square, ellipse, pentagon, hexagon, heptagon, octagon, star-shape, and cross-shape.
Figure 5B:
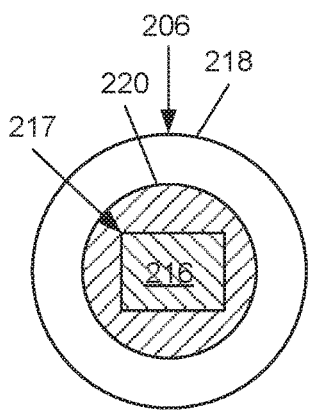
Figure 5C:
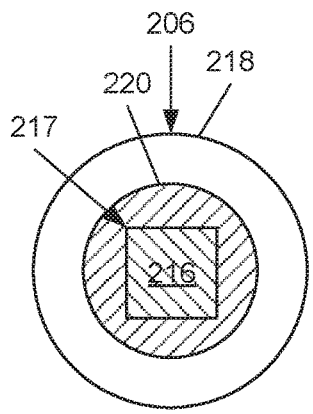
Figure 5D:
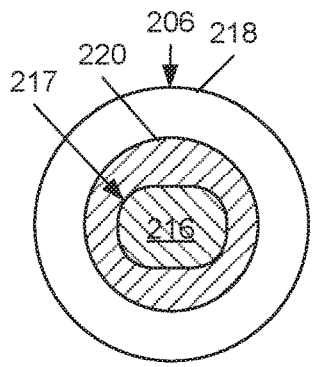
Figure 5E:
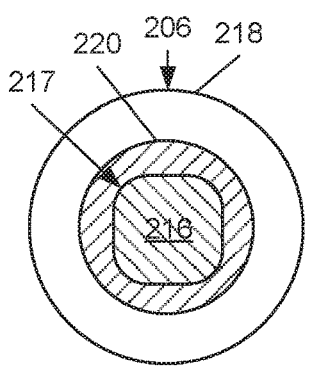
Figure 5F:
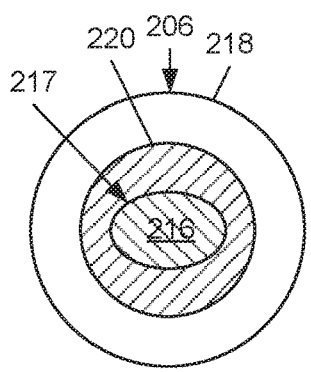
Figure 5G:
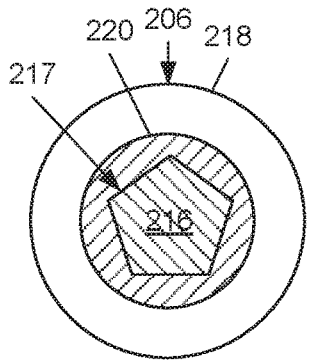
Figure 5H:
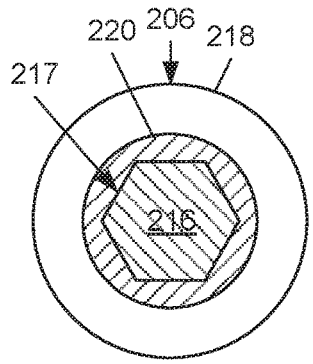
Figure 5I:
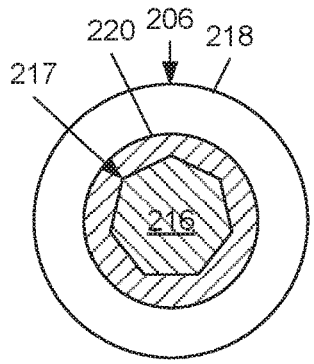
Figure 5J:
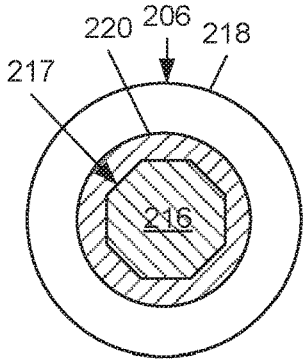
Figure 5K:
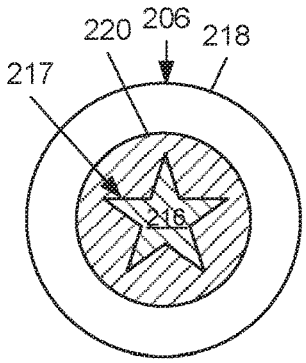
Figure 5L:
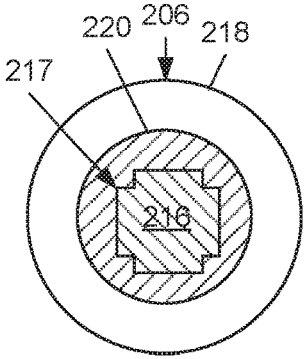
Figure 5P:
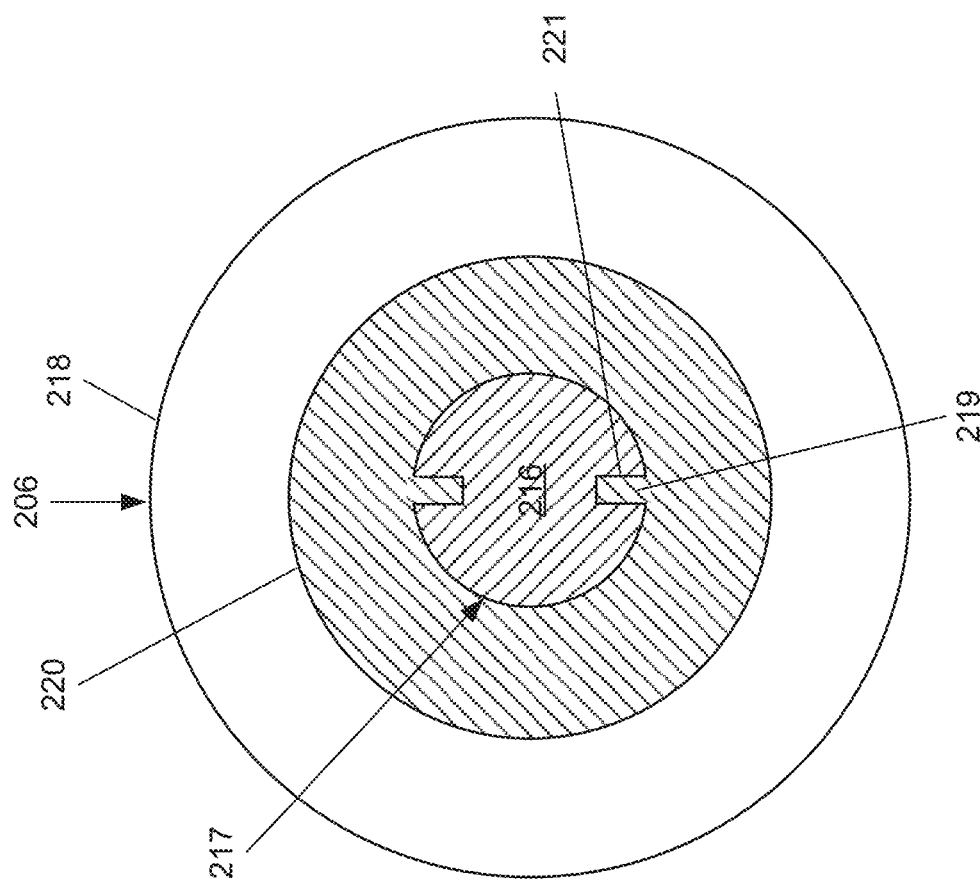
Figure 5O:
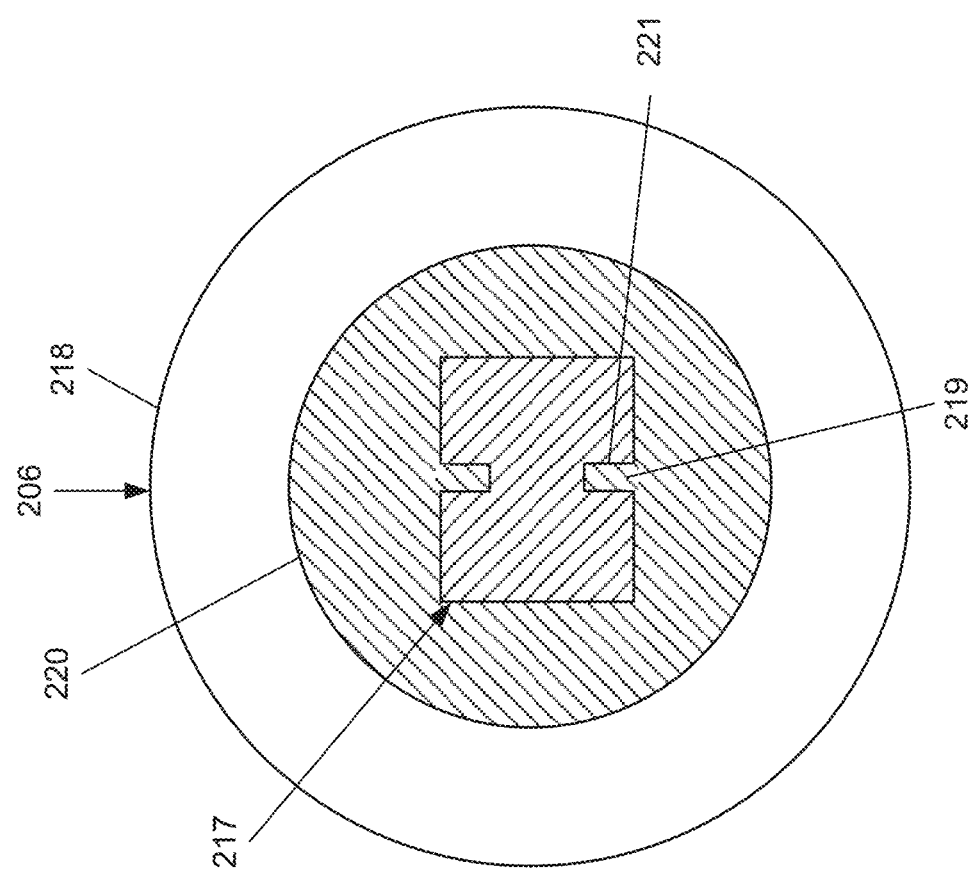

As shown in FIGS. 5M-5P, in one embodiment, the shaft 216 and the rotation limiter 206 includes a keyed interface that allows the rotation limiter to slide distal-proximal along the shaft but results in the shaft and rotation limiter rotating together as a unit. For example, as indicated in FIGS. 5M-5P, the keyed interface may include a male-female interface including a male feature 219 on one of the shaft or rotation limiter and a female feature 221 on the other of the shaft or rotation limiter, the male feature 219 being received in the female feature 221. Specifically, with respect to this male-female interface, in one embodiment as shown in FIGS. 5M and 5N, the shaft 216 could include one or more fins 219 extending along the shaft 216, and the rotation limiter 206 could include a corresponding number of slots 221, each slot receiving a respective fin. Of course, as depicted in FIGS. 50-5P, the arrangement could be reversed with the slot(s) 221 located on the shaft 216, and the corresponding fin(s) 219 located on the rotation limiter 206.

As indicated in FIG. 4 and FIGS. 5A-5P, the rotation limiter 206 includes a proximal flange 218 and a distal threaded barrel 220 distally extending from the proximal flange 218. The outer circumferential surface of the distal threaded barrel 220 supports a helical thread arrangement 222. The shaft 216 extends through a central opening or hole 217 in the rotation limiter 206 that extends distal-proximal through the rotation limiter. As already discussed above, the central opening or hole 217 of the rotation limiter 206 and the shaft 216 of the torque portion 204 are structurally interfaced such that the rotation limiter can slide distal-proximal along the shaft but results in the shaft and rotation limiter rotating together as a unit when the torque portion 204 is caused to rotate about its central longitudinal axis in driving the reset mechanism 200, which in turn drives the direct drive mechanism 214, which transitions the rotational displacement provided by the torque portion 204 into the displacement needed to transition the attachment mechanism 122 between the engaged and released states described above with respect to FIGS. 2-3D.

Figure 6:
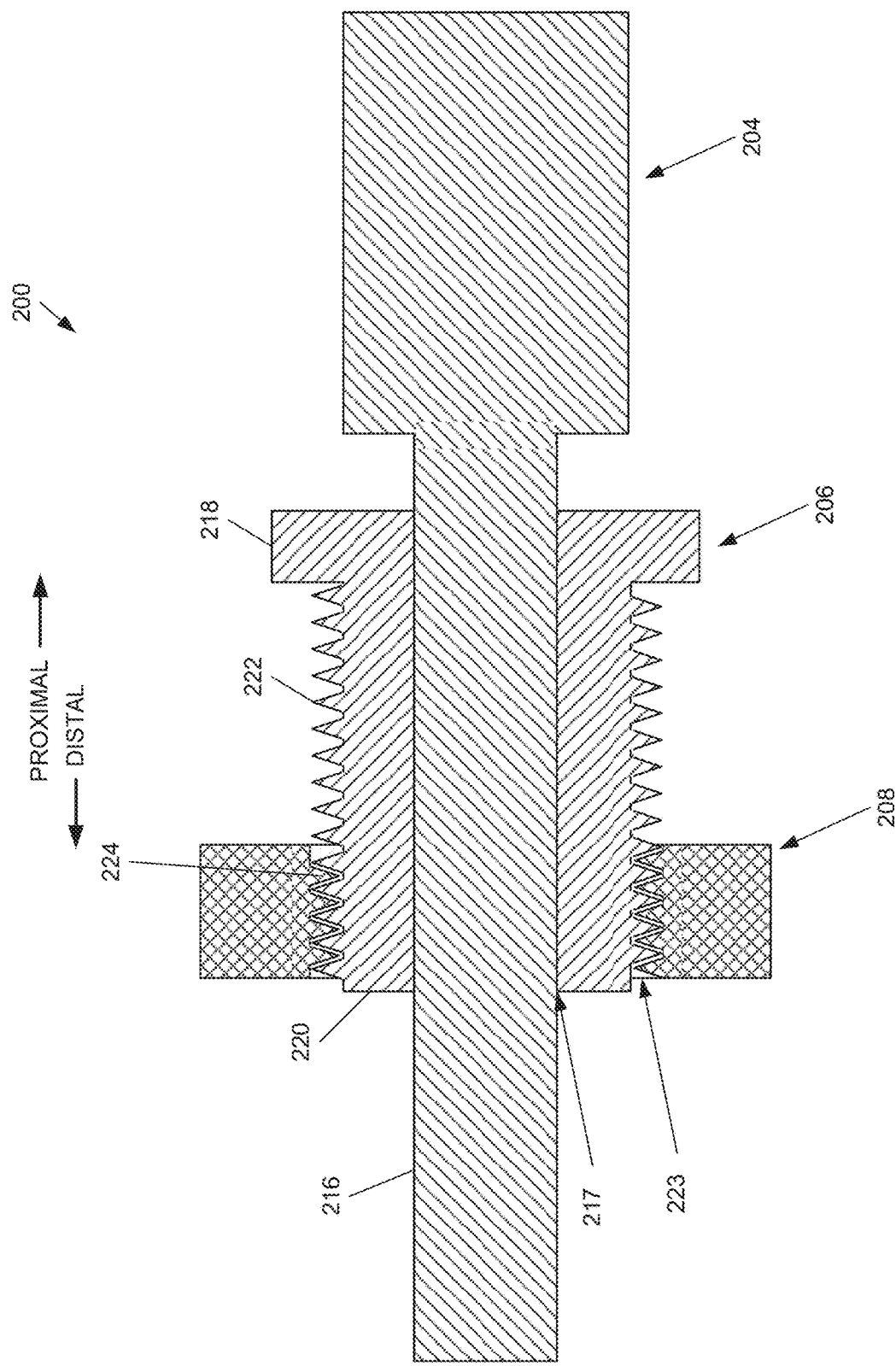
FIG. 6 is a longitudinal cross-section through torque portion, rotation limiter and threaded receptacle of the reset mechanism as taken along section line 6-6 in FIG. 4.

FIG. 6 is a longitudinal cross-section through the torque portion 204, rotation limiter 206 and threaded receptacle 208 of the reset mechanism 200 as taken along section line 6-6 in FIG. 4. As illustrated in FIG. 6, the shaft 216 of the torque portion 204 extends through the hole 217 of the rotation limiter 206 in the sliding, but non-rotating engagement described above with respect to FIGS. 5A-5P. The distal threaded barrel 220 extends through a threaded hole 223 of the threaded receptacle 208. The helical thread arrangement 222 of the threaded barrel 220 is in threaded engagement with the helical thread arrangement 224 of the threaded hole 223 of the threaded receptacle 208.

Figure 7:
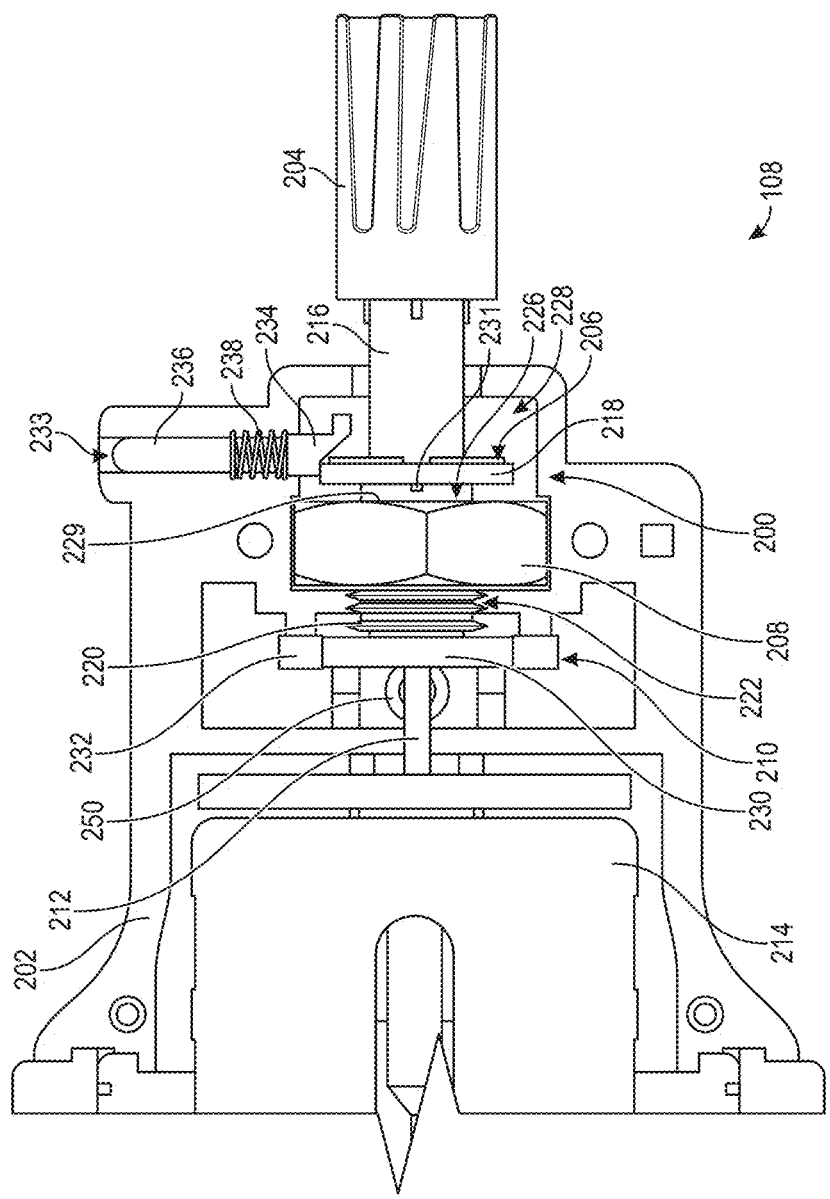
FIG. 7 is plan views of the proximal region of the handle of the leadless pacemaker delivery system of FIG. 1 with a portion of the housing of the handle removed to reveal the components of the reset mechanism contained therein and the rotation limiter abutting a distal stop limit.
Figure 8:
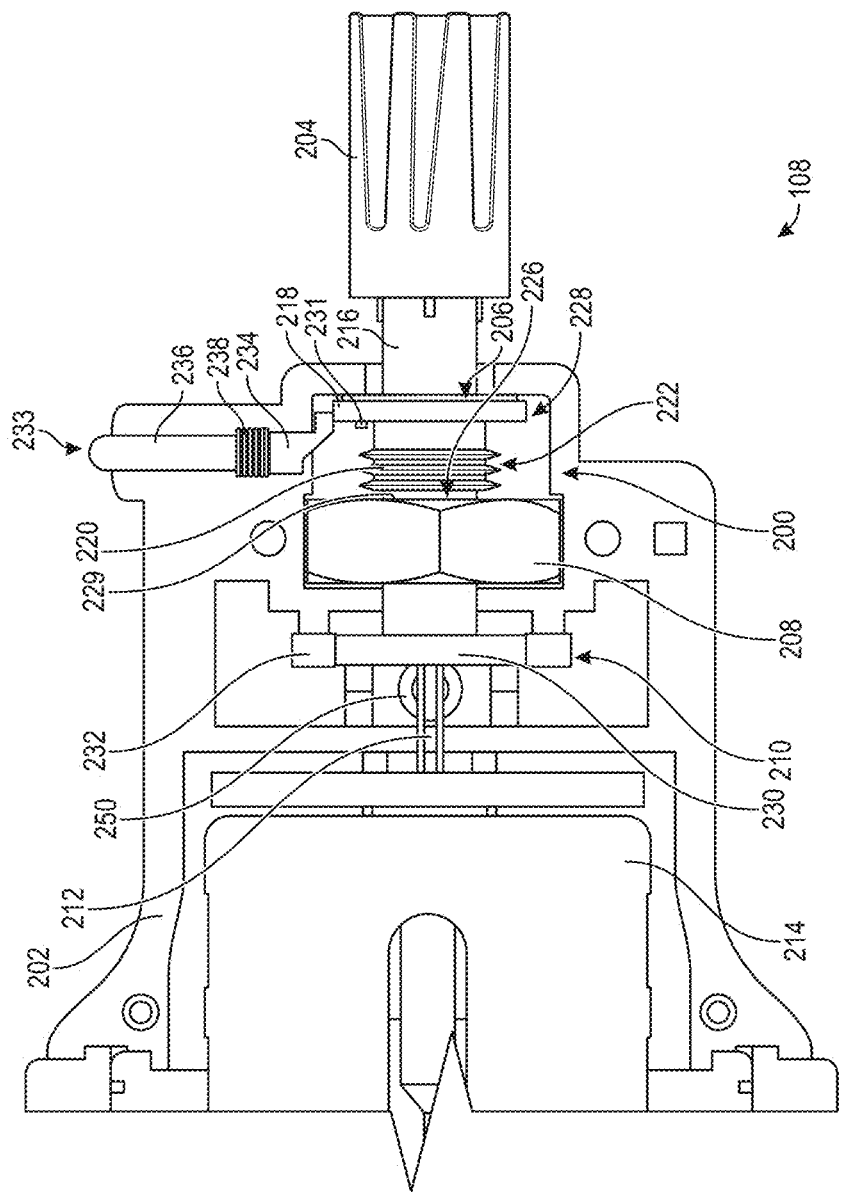
FIG. 8 is the same view as FIG. 7, except the rotation limiter is abutting a distal stop limit.

FIGS. 7 and 8 are plan views of the proximal region of the handle 108 of the leadless pacemaker delivery system 100 of FIG. 1 with a portion of the housing 202 of the handle 108 removed to reveal the components of the reset mechanism 200 contained therein. As can be understood from FIGS. 4 and 6-8, due to the threaded engagement between the threads 222, 224, the threaded receptacle 208 being fixed relative to the housing 202, and the rotation limiter 206 being slidable along, but non-rotatable relative too, the shaft 216, rotation of the torque portion 204 in a first direction (e.g., clockwise (CW)) causes the rotation limiter to move distally along the shaft 216, and rotation of the torque portion 204 in a second direction (e.g., counter-clockwise (CCW)) causes the rotation limiter to move proximally along the shaft 216.

As depicted in FIGS. 6 and 7, the rotation limiter 206 slides along the shaft 216 between a distal stop 226 and a proximal stop 228. For example, rotation of the torque portion 204 in a first direction to cause the attachment mechanism 122 (see FIGS. 2-3D) to assume the released state will cause the rotation limiter 206 to distally slide along the shaft 216 until a distal face of the flange 218 of the rotation limiter 206 abuts against a proximal face of the threaded receptacle 208, which acts as a distal stop limiter 226 for the rotation limiter 206, thereby preventing the rotation limiter 206 from further distally displacing along the shaft 216 and, as a result, inhibiting further rotation of the torque portion 204 in the first direction. Thus, further actuation of the attachment mechanism 122 (see FIGS. 2-3D) is positively stopped at a most optimal configuration of the released state.

In some embodiments, the distal stop 226, proximal stop 228 and/or the rotation limiter 206 may include features that allow for the distal and proximal stop limits of the reset mechanism 200 to be tuned such that the stop limits correspond to the most optimal configurations of the released and engaged states of the attachment mechanism. For example, the distal-proximal location of the distal stop 226 may be adjustable within the confines of the housing 202 or adapted such that it can be adjusted relative to the rest of the threaded receptacle 208. Similarly, the distal-proximal location of the proximal stop 228 may be adjustable within the confines of the housing 202 or adapted such that it can be adjusted relative to the rest of the housing 202. In the case of the rotation limiter 206, the proximal and distal faces of the flange 218 may be configured to be adjustable proximal-distal relative to the rest of the rotation limiter 206. By adjusting the proximal-distal location of the abutting aspects of the stops 226, 228 and/or the faces of the flange 218, the proximal-distal location of abutment between the flange faces and the stops 226, 228 can be tuned to correspond to the optimal released and engaged states of the attachment mechanism.

In some embodiments, as indicated in FIGS. 7 and 8, the distal or proximal stop limiter may take the form of, or be supplemented by, a capture feature 229 at or defined in the proximal face of the threaded receptacle 208. Depending on the direction the rotation limiter 206 designed to rotate in approaching a stop limiter and which stop limiter is being approached, the capture feature 229 may be designed to capture the tab 231 of the rotation limiter 206 rotating clockwise or counter-clockwise. The capture feature 229 may be a recess or similar pocket structure that receives a tab 231 distally protruding from the distal face of the flange 218 of the rotation limiter 206 when the distal face of the flange 218 is in such close proximity to the proximal face of the threaded receptacle 208 that the tab 231 can be received in the capture feature 229. The tab 231 being received in the capture feature 229 arrests the rotation of the rotation limiter 206 and the torque portion 204.

Depending on the embodiment, the capture feature 229 may be a series of capture features (e.g., indents) that provide tactile feedback to the user that the stop-limit is approaching. Similar function can be electronically achieved via, for example, an increase in resistance or other electronic feedback.

Figure 9:
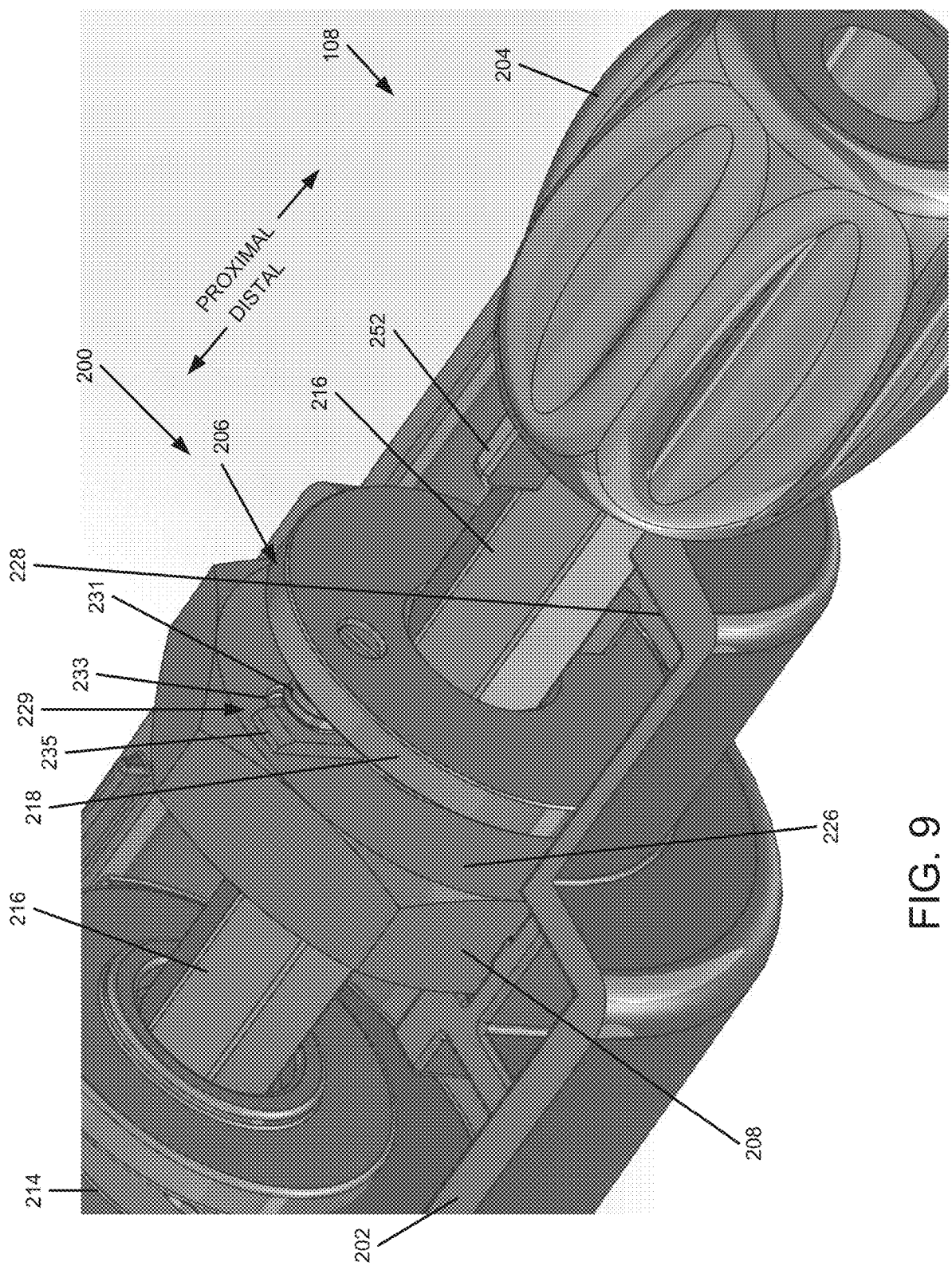
FIG. 9 is another isometric view of the proximal region of the handle of the leadless pacemaker delivery system of FIG. 1, wherein the rotation limiter is arrested in further rotation due to a tab of the rotation limiter being received in a capture feature of a threaded receptacle forming the distal stop limit.
Figure 10:
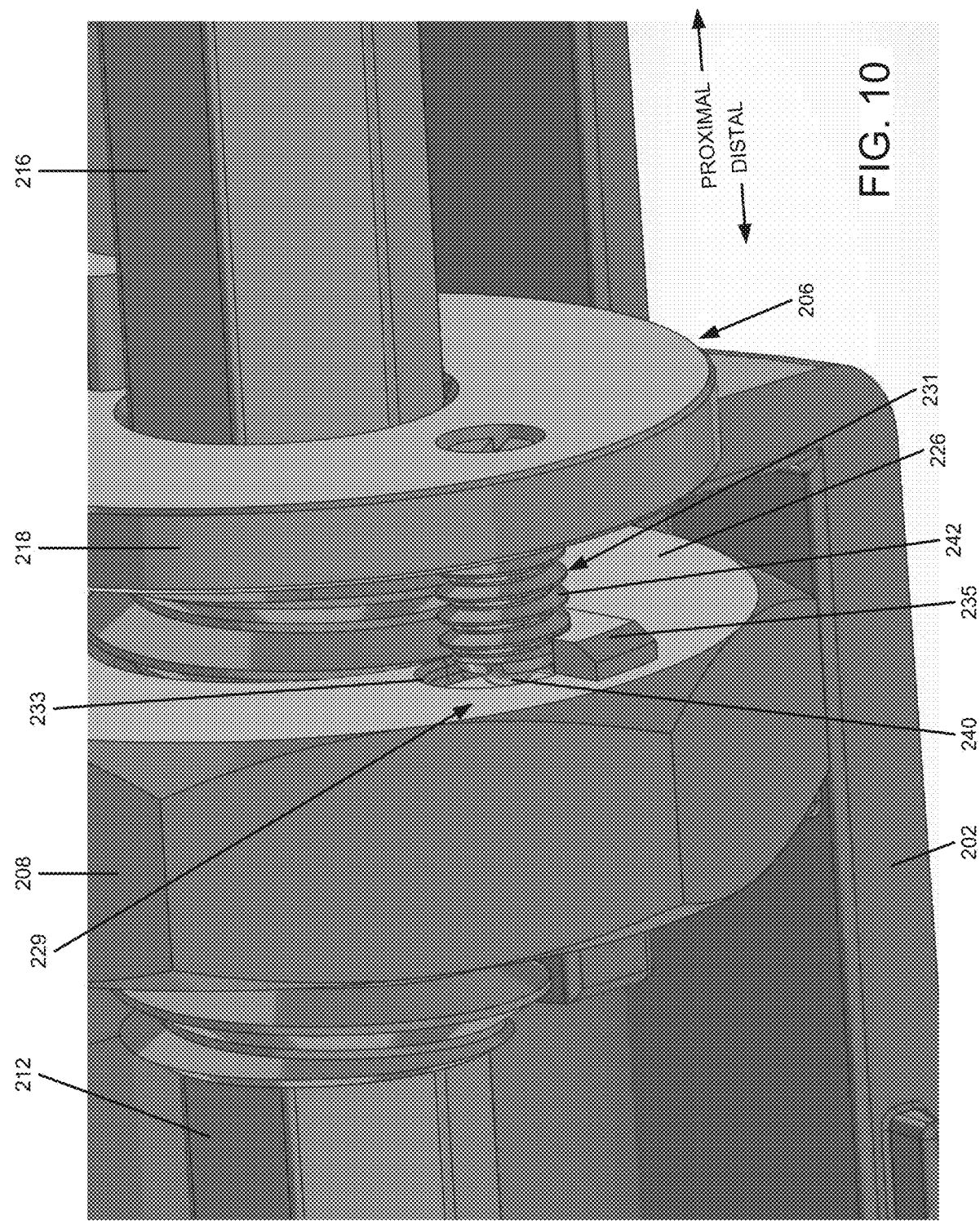
FIG. 10 is an enlarged isometric view of the tab received in the capture feature.

In some embodiments, as indicated in FIGS. 7 and 8 and more clearly depicted in FIGS. 9 and 10, the distal stop limiter 226 may take the form of, or be supplemented by, a capture feature 229 at or defined in the proximal face of the threaded receptacle 208. The capture feature 229 may include a recess 233 or similar pocket structure that receives a tab 231 distally protruding from the distal face of the flange 218 of the rotation limiter 206 when the distal face of the flange 218 is in such close proximity to the proximal face of the threaded receptacle 208 that the tab 231 can be received in the recess 233 of the capture feature 229. The tab 231 being received in the recess 233 of the capture feature 229 arrests the rotation of the rotation limiter 206 and the torque portion 204. Alternatively or additionally, the capture feature 229 may also include a raised lip or ridge 235 that is abutted by the tab 231 to arrest the rotation of the rotation limiter 206 and torque portion 204.

Figure 11:
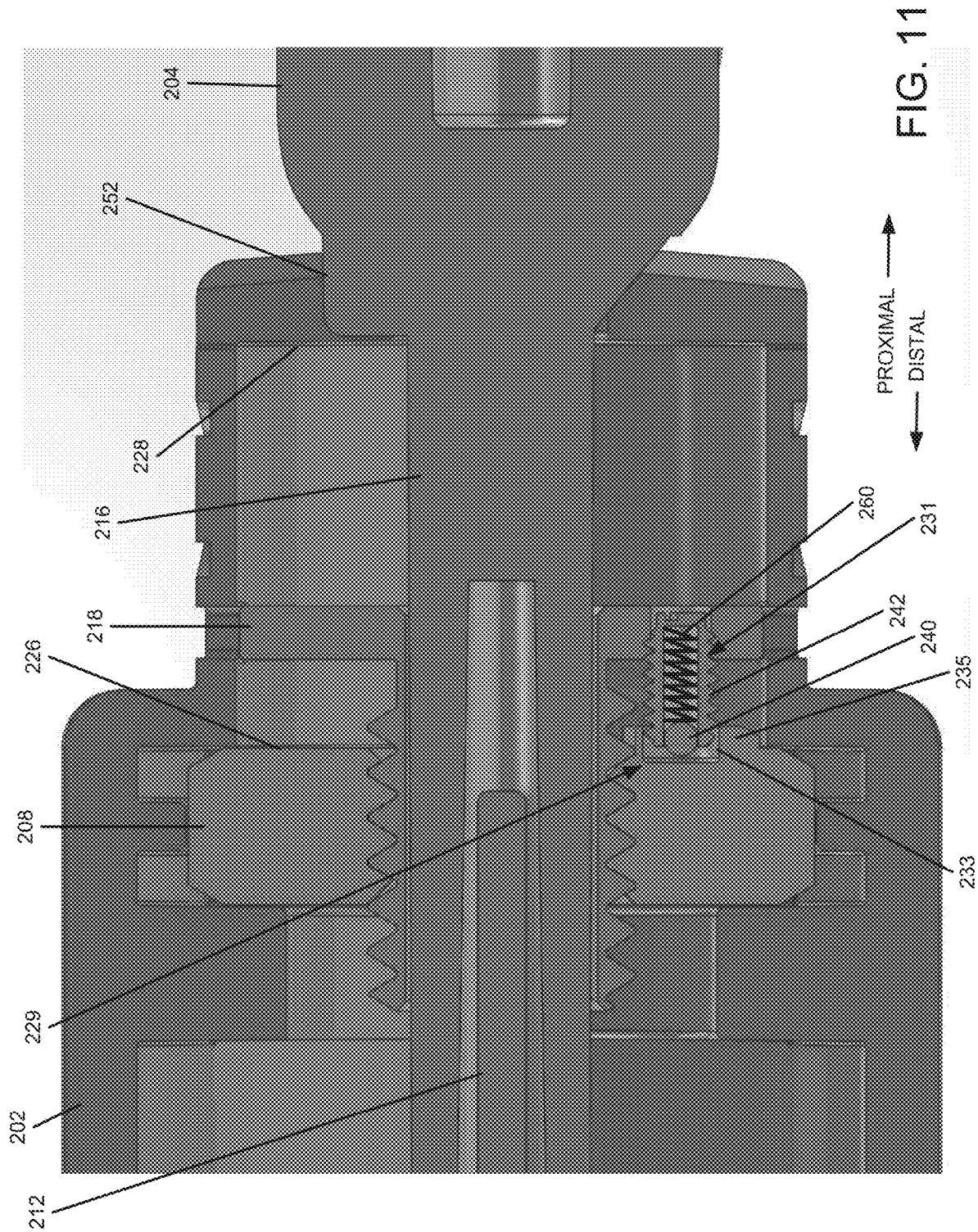
FIG. 11 is a longitudinal cross-section through reset mechanism and, specifically, the tab received in the capture feature.

In some embodiments, as depicted in FIGS. 10 and 11, the tab 231 may include a detent ball 240 and a cylindrical detent body 242. The detent ball 240 forms the distal tip of the tab 231 and is biased distally via a helical spring 260 (or other biasing member) within the distal confines of the cylindrical detent body 242 of the tab 231. The cylindrical detent body 242 is threadably attached to the flange 218 of the rotation limiter 206. The detent ball 240 is biased distally into the recess 233 of the capture feature 229 when the tab 231 is arrested by the capture feature 229, this detent feature helping to prevent the rotation limiter 206 from inadvertently backing away from its abutment with the distal stop 226.

As another example, rotation of the torque portion 204 in a second direction opposite the first direction to cause the attachment mechanism 122 (see FIGS. 2-3D) to assume the engaged state will cause the rotation limiter 206 to proximally slide along the shaft 216 until a proximal face of the flange 218 of the rotation limiter 206 abuts against a distal surface of the housing 202 of the handle 108. This abutment acts as a proximal stop limiter 228 for the rotation limiter 206, thereby preventing the rotation limiter 206 from further proximally displacing along the shaft 216 and, as a result, inhibiting further rotation of the torque portion 204 in the second direction. Thus, further actuation of the attachment mechanism 122 (see FIGS. 2-3D) is positively stopped at a most optimal configuration of the engaged state.

As shown in FIGS. 4, 7 and 8, the ratchet mechanism 210 is enclosed in the housing 202 and includes a disk 230 and pawl arms 232. The disk 230 is supported on, and rotated by, the drive shaft 212. As the disk 230 is caused to rotate via the rotation of the torque portion 204, the pawls arms 232 ratchet along the textured or contoured shape of the radial edge of the disk 230 to provide both a tactile indication and a segmented or stepped rotational displacement of the torque portion 204.

As shown in FIG. 4, just distal of the ratchet mechanism 210 is a retraction detent 250. The shaft 216 of the torque portion 204 is distally-proximally displaceable relative to the housing 202 and the rotation limiter 206. The disk 230 is fixedly connected to the distal end of the shaft 216 and can be distally-proximally displaced along the drive shaft 212 with the torque portion shaft 204. In doing so, the proximal region of the drive shaft 212 can be received in the distal confines of the disc 230 and torque portion shaft 204 to which the drive shaft is rotationally fixed, but distally-proximally slideable, when the torque portion shaft 230 and disc 230 are distally displaced relative to the housing 202. As the torque portion shaft 230 and disc 230 distally displace along the drive shaft 212, the disc 230 move distally from between the pawl arms 232 of the ratchet mechanism 210 such that the circumferential edge of the disc 230 becomes positioned over the retraction detent 250. Rotation of the torque portion 204 causes the disc 230, when distally positioned as described, to engage the retraction detent 250, thereby resulting in a tactile sensation in the torque member 204.

This interaction of the disc 230 and retraction detent 250 acts as a safety-interlock feature to prevent a user from inadvertently turning the release knob 204. Specifically, the safety-interlock feature forces the user to do the two following actions to achieve release of the mechanism: (1) retract the torque portion 204 with a force to overcome the retraction detent 250; and (2) rotate against a force set by the retraction detent 250 acting against the edge geometry of the disc 230.

As indicated in FIG. 4, the torque portion 204 also includes fins 252 that extend from the shaft 216. These fins 252 may be received in complementary slots (not shown) defined in the housing 202 such that, when the torque portion 204 is distally displaced from its proximal location indicated in FIG. 4, the fins 252 can be received in the housing slots (not shown) to lock the torque portion 204 rotationally relative to the housing 202.

In one embodiment, the housing handle 108 includes a position indicator 233 configured to indicate when the rotation limiter 206 reaches at least one of the distal stop limiter 226 or proximal stop limiter 228. Such a position indicator may take a variety of forms including an axially sliding indicator, an electronic binary indicator, or a radially displacing indicator.

For example, as can be understood from FIGS. 7 and 8, in one embodiment, the position indicator 233 includes a cam configuration 234 that interacts with the rotation limiter 206 to indicate when the rotation limiter 206 has reached at least one of the distal stop limiter 226 or proximal stop limiter 228. Specifically, the cam configuration 234 is located inwardly to interface with the outer radial edge surface of the flange 218 of the rotation limiter 206. A rod portion 236 extending radially outward from the cam configuration 234 includes a biasing member 238 that acts between the housing 202 and the rod portion 236 to radially inwardly bias the rod portion and, by extension, the cam configuration against the outer radial edge surface of the flange of the rotation limiter 206. In one embodiment, the biasing member 238 may be in the form of a helical spring extending about the rod portion 236.

As can be understood from FIG. 7, when the flange 218 of the rotation limiter 206 is fully distally displaced, the angled surface of the cam configuration 234 allows the biasing member 238 to bias the rod portion 236 fully inward such that the tip of the rod portion is at least flush with the outer surface of the housing 202, if not recessed thereto. Oppositely and as can be understood from FIG. 8, when the flange 218 of the rotation limiter 206 is fully proximally displaced, the angled surface of the cam configuration 234 acts against the outer radial edge surface of the flange 218 to overcome the biasing member 238 such that the rod portion 236 projects outward from the outer surface of the housing 202.

As can be understood from FIGS. 1-4, the reloadable delivery system 100 could be employed as follows for a dual chamber implant. First, a sterile delivery system 100 and a first sterile leadless pacemaker 102 are unpackaged from their respective sterile packaging. The attachment mechanism 122 is placed in the released state (e.g., the tether snare (FIG. 2) is opened to its greatest optimized extent or the tether members 126a, 126b (FIG. 3B) are staggered such that the release tether 126b is proximal the set tether 126a in an optimized arrangement). Reaching the optimized released state is achieved by rotating the torque portion 204 in first direction until the rotation limiter 206 abuts against the first stop limiter 226.

With the attachment mechanism in the optimized released state, the leadless pacemaker is loaded onto the attachment mechanism after which the torque portion is rotated in the second direction until the rotation limiter 206 abuts the second stop limiter 228. When the rotation limiter abuts against the second stop limiter, the attachment mechanism will have reached the optimized engaged state (e.g., the tether snare (FIG. 2) is closed to its greatest optimized extent, thereby having docked the leadless pacemaker with the delivery system 100 or the tether members 126a, 126b (FIGS. 3C-3D) are even with each other such that the release tether 126b is side-by-side with the set tether 126a in an optimized arrangement and docking the leadless pacemaker with the delivery system).

The loaded leadless pacemaker and the delivery system on which it is loaded are percutaneously inserted into the vasculature of the patient and tracked to an implant site in the right ventricle. The delivery system is rotated about it longitudinal axis to screw the anchor 103 of the leadless pacemaker 102 into the cardiac tissue to anchor the leadless pacemaker to the implant site.

The reset mechanism 200 is actuated via the torque portion 204 to reset the attachment mechanism 122 to the optimized released state. The rotation limiter abutting the first stop limiter facilitates the implanter placing the attachment mechanism in the optimized released state. With the attachment mechanism in the released state, the delivery system can be decoupled from the implanted first leadless pacemaker and withdrawn from the patient.

A second sterile leadless pacemaker can then be removed from its sterile packaging and loaded onto the delivery system in a manner as already described with respect to the first leadless pacemaker. With the second leadless pacemaker loaded on the delivery system, the implantation process can be repeated for the second leadless pacemaker as already described with respect to the first leadless pacemaker, except the implant takes place in the right atrium. As with the implantation of the first leadless pacemaker, once the implant of the second leadless pacemaker is complete, the delivery system can be likewise decoupled from the implanted second leadless pacemaker and withdrawn from the patient. The delivery system may be disposed of at this point if no other leadless pacemakers need to be implanted or, of course, the process can be repeated with the same delivery system as many more times as required to deliver even more leadless pacemakers into the same patient.

While the above-described reset mechanism is discussed in the context of a leadless pacemaker delivery device, those skilled in the art will readily understand that the reset mechanism may be employed with other medical devices such as, for example, minimally invasive surgery (MIS) tools, including for example, endoscopic devices, laparoscopic devices, and similar devices. The reset mechanism may be employed with tools for the delivery and fixation of a standard implantable lead or for the delivery, fixation and/or actuation of other implantable devices. Example of actuating an implanted devices include turning on an implantable device, opening a valve, causing a device to change states, etc., wherein any of these actuations or operational settings may be achieved via capturing an element of the implanted device via the above-described attachment mechanisms caused to operate between an engaged state and a released state, the operation of the attachment mechanism being limited to an ideal or preferred engaged state and an ideal or preferred released state by operation of the distal and proximal stops interacting with the reset mechanism described in detail above.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A tool for delivering a leadless pacemaker, the tool comprising:
   a handle including a housing;
   an attachment mechanism operably coupled to the housing and configured to actuate between a released state and an engaged state, the released state being when the attachment mechanism assumes a condition that allows the leadless pacemaker to be unattached to the tool, and the engaged state being when the attachment mechanism assumes a condition that allows the leadless pacemaker to be attached to the tool;
   a torque portion operably coupled to the housing and rotatable relative to the housing to transition the attachment mechanism between the released and engaged states, the torque portion including a shaft;
   a rotation limiter displaceable relative to the shaft between a first stop and a second stop, the rotation limiter including a first helical thread and an unthreaded portion at one end of the rotation limiter, the unthreaded portion selectively contacting each of the first stop and the second stop; and
   a second helical thread in threaded engagement with the first helical thread and operably coupled to the housing, wherein rotation of the torque portion rotates the rotation limiter such that the first helical thread is rotated against the second helical thread, thereby driving the rotation limiter along the shaft between the first stop and the second stop.

2. The tool of claim 1, wherein the attachment mechanism reaches the released state when the rotation limiter reaches the first stop, and the attachment mechanism reaches the engaged state when the rotation limiter reaches the second stop.

3. The tool of claim 1, further comprising a drive mechanism supported by the housing and operably coupling the torque portion to the attachment mechanism.

4. The tool of claim 1, further comprising a ratchet mechanism that gives feedback when the torque portion is rotated.

5. The tool of claim 1, further comprising a position indicator configured to indicate when the rotation limiter reaches at least one of the first stop or second stop.

6. The tool of claim 5, wherein the position indicator includes a cam configuration that interacts with the rotation limiter to indicate when the rotation limiter has reached at least one of the first stop or second stop.

7. The tool of claim 5, wherein the position indicator includes at least one of an axially sliding indicator, an electronic binary indicator, or a radially displacing indicator.

8. The tool of claim 1, wherein the shaft includes a transverse cross-section including a non-circular outer surface along which the rotation limiter can slide in displacing relative to the shaft between the first stop and the second stop, but linking the shaft and the rotation limiter together to rotate together as a unit.

9. The tool of claim 8, wherein the shaft extends through a hole in the rotation limiter, the hole including a shape that is a negative of the non-circular outer surface.

10. The tool of claim 8, wherein the non-circular outer surface of the transverse cross-section is in the form of one of an ellipse, square, rectangle, trapezoid, diamond, triangle, pentagon, hexagon, or octagon.

11. The tool of claim 1, wherein the shaft and the rotation limiter include a keyed interface that allows the rotation limiter to slide along the shaft in displacing relative to the shaft between the first stop and the second stop, but results in the shaft and rotation limiter rotating together as a unit.

12. The tool of claim 11, wherein the keyed interface includes a non-circular outer transverse cross-section of the shaft and a complementary negative surface of the rotation limiter that interfaces with the non-circular outer transverse cross-section of the shaft.

13. The tool of claim 11, wherein the keyed interface includes a male-female interface including a male feature on one of the shaft or rotation limiter and a female feature on the other of the shaft or rotation limiter, the male feature being received in the female feature.

14. The tool of claim 1, wherein the attachment mechanism includes a tether snare that has a first diameter when the attachment mechanism is in the released state and a second diameter when the attachment mechanism is in the engaged state, the second diameter being smaller than the first diameter.

15. The tool of claim 1, wherein the attachment mechanism includes a pair of tethers, each tether including a tether member, wherein the tether members are longitudinally offset from each other when the attachment mechanism is in the released state and the tether members are longitudinally even with each other and in a side-by-side arrangement when in the attachment mechanism is in the engaged state.

16. A medical tool configured to deliver a leadless pacemaker to an implantation site in a patient, the tool comprising:
- a handle including a housing;
- an elongated body distally extending from the handle;
- an attachment mechanism near a distal end of the elongated body and configured to actuate between a first state and a second state, wherein, when the attachment mechanism is in the first state, the attachment mechanism is configured to secure the leadless pacemaker to the tool, and when the attachment mechanism is in the second state, the attachment mechanism is configured such that the leadless pacemaker will not secure to the tool;
- a torque portion operably coupled to the housing and rotatable relative to the housing to transition the attachment mechanism between the first and second states, the torque portion including a shaft;
- a rotation limiter including a first helical thread and an unthreaded portion, the rotation limiter interfacing with the shaft such that the rotation limiter can slide along the shaft between a first stop and a second stop, but the shaft and the rotation limiter rotate together as a unit, the unthreaded portion selectively contacting each of the first stop and the second stop; and
- a second helical thread in threaded engagement with the first helical thread and fixed relative to the housing,
- wherein rotation of the torque portion rotates the rotation limiter such that the first helical thread is rotated against the second helical thread, thereby driving the rotation limiter along the shaft between the first stop and the second stop.

17. The tool of claim 16, wherein the attachment mechanism reaches the first state when the rotation limiter reaches the first stop, and the attachment mechanism reaches the second state when the rotation limiter reaches the second stop.

18. The tool of claim 16, further comprising a position indicator configured to indicate when the rotation limiter reaches at least one of the first stop or second stop.

19. The tool of claim 16, wherein the interfacing between the shaft and the rotation limiter includes a non-circular outer transverse cross-section of the shaft and a complementary negative surface of the rotation limiter that interfaces with the non-circular outer transverse cross-section of the shaft.

20. The tool of claim 16, wherein the interfacing between the shaft and the rotation limiter includes a male-female arrangement including a male feature on one of the shaft or rotation limiter and a female feature on the other of the shaft or rotation limiter, the male feature being received in the female feature.

21. The tool of claim 16, wherein the attachment mechanism includes a tether snare that has a first diameter when the attachment mechanism is in the first state and a second diameter when the attachment mechanism is in the second state, the second diameter being larger than the first diameter.

22. The tool of claim 16, wherein the attachment mechanism includes a pair of tethers, each tether including a tether member, wherein the tether members are longitudinally offset from each other when the attachment mechanism is in the second state and the tether members are longitudinally even with each other and in a side-by-side arrangement when in the attachment mechanism is in the first state.

* * * * *